United States Patent
Bischoff et al.

(10) Patent No.: US 10,112,943 B2
(45) Date of Patent: Oct. 30, 2018

(54) SUBSTITUTED IMIDAZOLES AS GAMMA SECRETASE MODULATORS

(71) Applicant: Janssen Pharmaceutica NV, Beerse (BE)

(72) Inventors: François Paul Bischoff, Beerse (BE); Henricus Jacobus Maria Gijsen, Beerse (BE); Frans Alfons Maria Van den Keybus, Beerse (BE); Frederik Jan Rita Rombouts, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/654,397

(22) PCT Filed: Dec. 19, 2013

(86) PCT No.: PCT/EP2013/077425
§ 371 (c)(1),
(2) Date: Jun. 19, 2015

(87) PCT Pub. No.: WO2014/096212
PCT Pub. Date: Jun. 26, 2014

(65) Prior Publication Data
US 2015/0307496 A1    Oct. 29, 2015

(30) Foreign Application Priority Data

Dec. 20, 2012 (EP) .................................. 12198403

(51) Int. Cl.
*A61K 31/4178* (2006.01)
*C07D 233/54* (2006.01)
*C07D 471/14* (2006.01)

(52) U.S. Cl.
CPC ................................. *C07D 471/14* (2013.01)

(58) Field of Classification Search
CPC ........................ A61K 31/4178; C07D 233/54
USPC ....................... 514/397; 544/344; 548/335.1
See application file for complete search history.

(56) References Cited

U.S. PATENT DOCUMENTS

| | | | |
|---|---|---|---|
| 5,565,453 A | 10/1996 | Bright et al. |
| 5,767,144 A | 6/1998 | Winn et al. |
| 6,114,334 A | 9/2000 | Kerrigan et al. |
| 6,995,155 B2 | 2/2006 | Churcher et al. |
| 7,517,532 B2 | 4/2009 | Wai et al. |
| 7,923,563 B2 | 4/2011 | Kushida et al. |
| 8,598,353 B2 | 12/2013 | Mjalli et al. |
| 8,664,411 B2 | 3/2014 | Wu et al. |
| 8,916,564 B2 | 3/2014 | Pettersson et al. |
| 2002/0128319 A1 | 9/2002 | Galasko et al. |
| 2006/0004013 A1 | 1/2006 | Kimura et al. |
| 2006/0223849 A1 | 10/2006 | Mjalli et al. |
| 2008/0280948 A1 | 11/2008 | Baumann et al. |
| 2009/0062529 A1 | 3/2009 | Doko et al. |
| 2010/0137320 A1 | 6/2010 | Huang et al. |
| 2011/0015175 A1 | 1/2011 | Marchin et al. |
| 2012/0053165 A1 | 3/2012 | Allen et al. |

FOREIGN PATENT DOCUMENTS

| | | |
|---|---|---|
| CA | 2118936 A1 | 4/2001 |
| CN | 101142194 | 3/2008 |
| EP | 1757591 | 2/2007 |
| EP | 1992618 A1 | 11/2008 |
| JP | 2003/502313 | 1/2003 |
| WO | WO 01/78721 | 10/2001 |
| WO | WO 01/87845 | 11/2001 |
| WO | WO 02/22574 | 3/2002 |
| WO | WO 2002/069946 | 9/2002 |
| WO | WO 04/024078 | 3/2004 |
| WO | WO 2004/017963 | 3/2004 |
| WO | WO 2004/076448 | 9/2004 |
| WO | WO 2004/110350 | 12/2004 |
| WO | WO 2005/016892 | 5/2005 |
| WO | WO 2005/085245 | 9/2005 |
| WO | WO 2005/115990 | 12/2005 |

(Continued)

OTHER PUBLICATIONS

Jordan, V. C. Nature Reviews: Drug Discovery, 2, 2003, 205-213.*

(Continued)

*Primary Examiner* — Douglas M Willis

(57) ABSTRACT

The present invention is concerned with novel tricyclic 3,4-dihydro-2H-pyrido[1,2-a]pyrazine-1,6-dione derivatives of Formula (I)

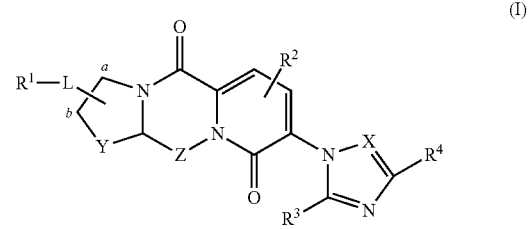

wherein $R^1$, $R^2$, $R^3$, $R^4$, L, Y, Z and X have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

14 Claims, No Drawings

(56) References Cited

FOREIGN PATENT DOCUMENTS

| | | |
|---|---|---|
| WO | WO 2006/099379 | 9/2006 |
| WO | WO 2006/135667 | 12/2006 |
| WO | WO 2007/034252 | 3/2007 |
| WO | WO 2007/038314 | 4/2007 |
| WO | WO 2007/043786 | 4/2007 |
| WO | WO 2007/044895 | 4/2007 |
| WO | WO 2007/058942 | 5/2007 |
| WO | WO 2007/102580 | 9/2007 |
| WO | WO 2007/105053 | 9/2007 |
| WO | WO 2007/113276 | 10/2007 |
| WO | WO 2007/131991 | 11/2007 |
| WO | WO 2008/065199 | 6/2008 |
| WO | WO 2008/073370 | 6/2008 |
| WO | WO 2008/082490 | 7/2008 |
| WO | WO 2008/097538 | 8/2008 |
| WO | WO 2008/099210 | 8/2008 |
| WO | WO 2008/100412 | 8/2008 |
| WO | WO 2008/137139 | 11/2008 |
| WO | WO 2008/156580 | 12/2008 |
| WO | WO 2009/005729 | 1/2009 |
| WO | WO 2009/028588 | 3/2009 |
| WO | WO 2009/032277 | 3/2009 |
| WO | WO 2009/050227 | 4/2009 |
| WO | WO 2009/073777 | 6/2009 |
| WO | WO 2009/076352 | 6/2009 |
| WO | WO 2009/103652 | 8/2009 |
| WO | WO 2009/155551 | 12/2009 |
| WO | WO 2010/010188 | 1/2010 |
| WO | WO 2010/052199 A1 | 5/2010 |
| WO | WO 2010/054067 | 5/2010 |
| WO | WO 2010/065310 | 6/2010 |
| WO | WO 2010/070008 | 6/2010 |
| WO | WO 2010/083141 | 7/2010 |
| WO | WO 2010/089292 | 8/2010 |
| WO | WO 2010/094647 | 8/2010 |
| WO | WO 2010/098487 | 9/2010 |
| WO | WO 2010/098488 | 9/2010 |
| WO | WO 2010/098495 | 9/2010 |
| WO | WO 2010/100606 | 9/2010 |
| WO | WO 2010/106745 | 9/2010 |
| WO | WO 2010/114971 | 10/2010 |
| WO | WO 2010/126745 | 11/2010 |
| WO | WO 2010/137320 | 12/2010 |
| WO | WO 2010/145883 | 12/2010 |
| WO | WO 2011/006903 | 1/2011 |
| WO | WO 2011/048525 | 4/2011 |
| WO | WO 2011/086098 | 7/2011 |
| WO | WO 2011/086099 | 7/2011 |
| WO | WO 2011/094823 | 8/2011 |
| WO | WO 2012/126984 | 9/2012 |
| WO | WO 2012/131539 | 10/2012 |
| WO | WO 2013/010904 | 1/2013 |
| WO | WO 2013/171712 | 11/2013 |
| WO | WO 2014/045156 | 3/2014 |
| WO | WO 2014/096212 * | 6/2014 |
| WO | WO 2014/111457 | 6/2014 |

OTHER PUBLICATIONS

Hackam, et al. JAMA, 296(14), 2006, 1731-1732.*
Citron et al (1997) Nature Medicine 3: 67.
Eriksen (2003) J. Clin. Invest. 112, 440.
Greene and P. G. M. Wuts in "Protective Groups in Organic Chemistry", John Wiley and Sons, 1999.
Lamer, 2004. Secretases as therapeutics targets in AD: patents 2000-2004. Expert Opin. Ther. Patents 14, 1403-1420.
Marjaux et al., 2004. Drug Discovery Today: Therapeutic Strategies, vol. 1, 1-6.
Peretto et al., 2005, J. Med. Chem. 48, 5705-5720.
Schweisguth F (2004) Curr. Biol. 14, R129.
Steiner, 2004. Curr. Alzheimer Research 1(3): 175-181.
Tanzi and Bertram, 2005, Cell 120, 545.
International Search Report for PCT/EP2013/077425 dated Feb. 6, 2014.
International Search Report for PCT/EP2014/050787 dated Feb. 21, 2014.
ACS Symposium Series, 870 (Chemical Process Research), Willemsens American Chemical Society, 125-139, 2004.
Li, Org. Lett. 2010, 12, 3332.
Waldvogel, Helv. Chim. Acta, 1992, 907.
"Crystallization", Kirk-Othmer Encyclopedia of Chemical Technology, 2002, 8, 95-147.
Dorwald, "Side Reactions in Organic Synthesis", Wiley: VCH Weinheim Preface, Chapter 8, 45 pages.
Dyatkin et al., "Determination of the Absolute Configuration of a Key Tricyclic Component of a Novel Vasopressin Receptor Antagonist by Use of Vibrational Circular Dichroism", Chirality, 2002, 14, 215-219.
Garofalo, "Patents Targeting Gamma-Secretase Inhibition and Modulation for the Treatment of Alzheimer's Disease: 2004-2008", Expert Opinion Ther. Patents, 2008, 18(7), 693-703.
Guillory (Brittain Ed.). "Polymorphism in Pharmaceutical Solids" Marcel Dekker. Inc., NY, 1999, 50 pages.
International Patent Application No. PCT/EP2011/050350: International Search Report dated Feb. 23, 2011, 3 pages.
Jadhav et al. "Ammonium Metavanadate: a Novel Catalyst for Synthesis of 2-Substituted Benzimidazole Derivatives", Chinese Chemical Letters, 2009, 20, 292-295.
Jain et al., "Polymorphism in Pharmacy", Indian Drugs, 1986, 23(6), 315-329.
Matthews et al., "A Convenient Procedure for the Preparation of 4(5)-Cyanoimidazoles", J. Org. Chem., 1986 51, 3228-3231.
Moechars et al., "Early Phenotypic Changes in Transgenic Mice That Overexpress Different Mutants of Amyloid Precursor Protein in Brain", J. Biol. Chem., 1999, 274(10), 6483-6492.
Morihara et al., "Selective Inhibition of Aβ42 Production by NSAID R-Enantiomers", Journal of Neurochemistry, 2002, 83, 1009-1012.
Oumata et al., "Roscovitine-Derived, Dual-Specificity Inhibitors of Cyclin-Dependent Kinases and Casein Kinases 1", J. Med. Chem., 2008, 51, 5229-5242.
Sechi et al., "Design and Synthesis of Novel Indole β-Diketo Acid Derivatives as HIV-1 Integrase Inhibitors", J. Med. Chem., 2004, 47, 5298-5310.
Vippagunta et al., "Crystalline Solids", Advanced Drug Delivery Reviews, 2001, 48, 3-26.
Wang et al., "Preparation of a-Chloroketones by the Chloracetate Claisen Reaction", Synlett, 2000, 6, 902-904.
Weggen et al., "A Subset of NSAIDs Lower Amyloidegenic Aβ42 Independently of Cyclooxygenase Activity", Nature, Nov. 2001, 414, 212-216.
Wermuth, "Chapter 13 — Molecular Variations Based on Isosteric Replacements", The Practice of Medicinal Chemistry, 1996, 35 pages.
West, "Solid State Chemistry and its Applications", Wiley, New York, 1988, 16 pages (see pp. 358 & 365).
Yu et al. "Physical Characterization of Polymorphic Drugs: An Integrated Characterization Strategy", PSTT, 1998, 1(3), 118-127.
Zettl et al., "Exploring the Chemical Space of γ-Secretase Modulators" ,Trends in Pharmaceutical Sciences, 2010, 31(9), 402-410.
International Search Report for PCT/IB2013/054014 dated Aug. 20, 2013.
Notice of Allowance for U.S. Appl. No. 14/400,663 dated Jul. 17, 2015.
Office Action for U.S. Appl. No. 14/400,663 dated Apr. 14, 2015.
Jordan, V. C. Nature Reviews: Drug Discovery, 2, 2003, 205.
Sipo Search Report dated Mar. 16, 2016.
Office Action for (Application No. 201380066966.9) dated Apr. 5, 2016.
Office Action for (Application No. 2015-548580) dated Sep. 19, 2017.
Eimer et al., Neuron loss in the 5XFAD mouse model of Alzheimer's disease correlates with intraneuronal Aβ$_{42}$accumulation and Caspase-3 activation, Molecular Neurodegenaration , 2013, 8:2.

(56) References Cited

OTHER PUBLICATIONS

Arnold Reissert, Chemische Berichte, 30_1897_1030-1045 (English Translation).

* cited by examiner

SUBSTITUTED IMIDAZOLES AS GAMMA SECRETASE MODULATORS

CROSS REFERENCE TO RELATED APPLICATIONS

This application is the national stage of PCT Application No. PCT/EP2013/077425, filed Dec. 19, 2013, which claims priority from European Patent Application No. 12198403.3, filed Dec. 20, 2012, the entire disclosures of which are hereby incorporated in their entirety.

FIELD OF THE INVENTION

The present invention is concerned with novel tricyclic 3,4-dihydro-2H-pyrido-[1,2-a]pyrazine-1,6-dione derivatives useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major components of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Aβ is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in the region of a particular gene coding in a particular protein (presenilin), and these mutations have been correlated with early-onset familial AD. Therefore, Aβ42 is believed by many researchers to be the main culprit of the pathogenesis of AD.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of AD.

Various strategies have been proposed for targeting γ-secretase in AD, ranging from targeting the catalytic site directly, developing substrate-specific inhibitors and modulators of γ-secretase activity (Marjaux et al., 2004. Drug Discovery Today: Therapeutic Strategies, Volume 1, 1-6). Accordingly, a variety of compounds were described that have secretases as targets (Lamer, 2004. Secretases as therapeutics targets in AD: patents 2000-2004. Expert Opin. Ther. Patents 14, 1403-1420).

Indeed, this finding was supported by biochemical studies in which an effect of certain Non-Steroidal Anti-Inflammatory Drugs (NSAIDs) on γ-secretase was shown (US 2002/0128319; Eriksen (2003) J. Clin. Invest. 112, 440). Potential limitations for the use of NSAIDs to prevent or treat AD are their inhibition activity of cyclooxygenase (COX) enzymes, which can lead to unwanted side effects, and their low CNS penetration (Peretto et al., 2005, J. Med. Chem. 48, 5705-5720). More recently the NSAID R-flurbiprofen, an enantiomer lacking Cox-inhibitory activity and related gastric toxicity, has failed in large phase III trial since the drug did not improve thinking ability or the ability of patients to carry out daily activities significantly more than those patients on placebo.

WO-2010/100606 discloses phenyl imidazoles and phenyl triazoles for use as gamma-secretase modulators.

US20090062529 relates to polycyclic compounds effective as therapeutic or prophylactic agents for a disease caused by Aβ.

WO-2010/070008 is concerned with novel substituted bicyclic imidazole derivatives useful as γ-secretase modulators.

WO-2010/089292 is concerned with novel substituted bicyclic heterocyclic compounds useful as γ-secretase modulators.

WO-2011/006903 is concerned with novel substituted triazole and imidazole derivatives useful as γ-secretase modulators.

WO-2012/131539 relates to novel bicyclic pyridinones useful as brain-penetrable γ-secretase modulators.

There is a strong need for novel compounds which modulate γ-secretase activity thereby opening new avenues for the treatment of AD. It is an object of the present invention to overcome or ameliorate at least one of the disadvantages of the prior art, or to provide a useful alternative. The compounds of the present invention or part of the compounds of the present invention may have improved metabolic stability properties, improved central brain availability, improved solubilities, or reduced CYP inhibition compared with the compounds disclosed in the prior art. It is accordingly an object of the present invention to provide such novel compounds.

SUMMARY OF THE INVENTION

It has been found that the compounds of the present invention are useful as γ-secretase modulators. The compounds according to the invention and the pharmaceutically acceptable compositions thereof, may be useful in the treatment or prevention of AD.

The present invention concerns novel compounds of Formula (I)

tautomers and stereoisomeric forms thereof, wherein $R^1$ is phenyl, naphthyl, indolyl, benzothienyl, benzothiazolyl or benzofuranyl;
  each optionally substituted with one, two or three substituents each independently selected from the group consisting of halo and $C_{1-4}$alkyl optionally substituted with one, two or three halo substituents;

L is attached at position a or b;
  L is selected from the group consisting of a covalent bond, —$C_{1-6}$alkanediyl- and —O—$C_{1-6}$alkanediyl-;

Y is -Q-$(CH_2)_m$—, —$CH_2$-Q-$CH_2$—, —$(CH_2)_n$—,
  —$(CH_2)_n$— wherein one —$CH_2$— is substituted with hydroxyl and $C_{1-4}$alkyl, or
  —$(CH_2)_n$— wherein one —$CH_2$— is substituted with one hydroxyl;

n represents 1, 2 or 3;
m represents 1 or 2;
Q is O or $NR^6$;
$R^6$ is hydrogen or $C_{1-4}$alkyl;
Z is methylene or 1,2-ethanediyl, wherein methylene or 1,2-ethanediyl is optionally substituted with one or two $C_{1-4}$alkyl substituents;
$R^2$ is hydrogen, halo or $C_{1-4}$alkyl;
$R^3$ is hydrogen or $C_{1-4}$alkyl;
$R^4$ is hydrogen, halo or $C_{1-4}$alkyl;
X is $CR^5$ or N;
$R^5$ is hydrogen or $C_{1-4}$alkyl;

and the pharmaceutically acceptable addition salts, and the solvates thereof.

The present invention also concerns methods for the preparation of compounds of the present invention and pharmaceutical compositions comprising them.

The compounds of the present invention were found to modulate the γ-secretase activity in vitro and in vivo, and therefore may be useful in the treatment or prevention of AD, traumatic brain injury (TBI), dementia pugilistica, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid; preferably AD and other disorders with Beta-amyloid pathology (e.g. glaucoma).

In view of the aforementioned pharmacology of the compounds of Formula (I) and the pharmaceutically acceptable addition salts, and the solvates thereof, it follows that they may be suitable for use as a medicament.

More especially the compounds of Formula (I) and the pharmaceutically acceptable addition salts, and the solvates thereof, may be suitable in the treatment or prevention of AD, cerebral amyloid angiopath, multi-infarct dementia, dementia pugilistica and Down syndrome.

The present invention also concerns the use of compounds according to the general Formula (I), and the pharmaceutically acceptable acid or base addition salts and the solvates thereof, for the manufacture of a medicament for the modulation of γ-secretase activity.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

Whenever the term "substituted" is used in the present invention, it is meant, unless otherwise is indicated or is clear from the context, to indicate that one or more hydrogens, in particular from 1 to 3 hydrogens, preferably 1 or 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The term "halo" as a group or part of a group is generic for fluoro, chloro, bromo, iodo unless otherwise is indicated or is clear from the context.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, preferably from 1 to 3 carbon atoms, more preferably 1 to 2 carbon atoms. $C_{1-4}$alkyl groups may be linear or branched and may be substituted as indicated herein. When a subscript is used herein following a carbon atom, the subscript refers to the number of carbon atoms that the named group may contain. $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-6}$alkanediyl" as a group or part of a group defines bivalent straight or branched chained saturated hydrocarbon radicals having from 1 to 6 carbon atoms such as, for example, methylene or methanediyl, ethan-1,2-diyl, ethan-1,1-diyl or ethylidene, propan-1,3-diyl, propan-1,2-diyl, butan-1,4-diyl, pentan-1,5-diyl, pentan-1,1-diyl, hexan-1,6-diyl, 2-methylbutan-1,4-diyl, 3-methylpentan-1,5-diyl and the like.

Whenever variable 'L' represents —O—$C_{1-6}$alkanediyl-, it is intended that the oxygen is attached to '$R^1$' and $C_{1-6}$alkanediyl is attached to the remainder of the molecule in position a or b. This is illustrated by formula (I'):

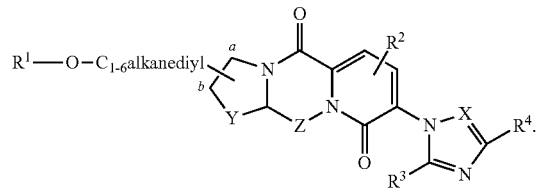

(I')

Whenever variable 'Y' represents -Q-$(CH_2)_m$—, it is intended that Q is attached to the carbon atom in position b and $(CH_2)_m$ is attached to ring fused carbon atom. This is illustrated by formula (I"):

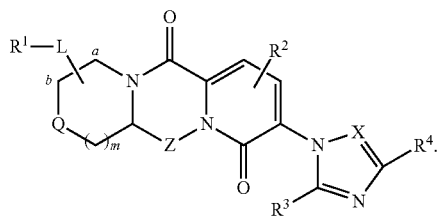

(I")

The chemical names of the compounds of the present invention were generated according to the nomenclature rules agreed upon by the Chemical Abstracts Service, using Advanced Chemical Development, Inc., nomenclature software (ACD/Labs Release 12.00 Product version 12.01: Build 33104, 27 May 2009). In case of tautomeric forms, the name of the depicted tautomeric form was generated. It should be clear that the other non-depicted tautomeric form is also included within the scope of the present invention.

In case L represents —$(CH_2)_n$—, n represents 1, and Z is methylene, the atoms in the tricyclic system are numbered as agreed upon by the Chemical Abstracts Service, as shown in the following formula (XX-a):

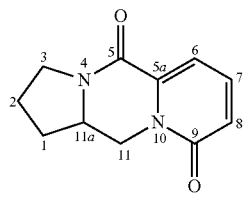

(XX-a)

In case L represents —$(CH_2)_n$—, n represents 2, and Z is methylene, the atoms in the tricyclic system are numbered as agreed upon by the Chemical Abstracts Service, as shown in the following formula (XX-b):

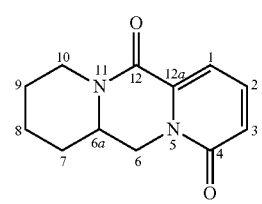

(XX-b)

The term "compounds of the invention" as used herein, is meant to include the compounds of Formula (I), and the salts and solvates thereof.

As used herein, any chemical formula with bonds shown only as solid lines and not as solid wedged or hashed wedged bonds, or otherwise indicated as having a particular configuration (e.g. R, S) around one or more atoms, contemplates each possible stereoisomer, or mixture of two or more stereoisomers.

Hereinbefore and hereinafter, the term "compound of Formula (I)" is meant to include the stereoisomers thereof and the tautomeric forms thereof.

The terms "stereoisomers", "stereoisomeric forms" or "stereochemically isomeric forms" hereinbefore or hereinafter are used interchangeably.

The invention includes all stereoisomers of the compounds of the invention either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. Substituents on bivalent cyclic (partially) saturated radicals may have either the cis- or trans-configuration; for example if a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof, whenever chemically possible.

The meaning of all those terms, i.e. enantiomers, diastereomers, racemates, E isomers, Z isomers, cis isomers, trans isomers and mixtures thereof are known to the skilled person.

The absolute configuration is specified according to the Cahn-Ingold-Prelog system.

The configuration at an asymmetric atom is specified by either R or S. Resolved stereoisomers whose absolute configuration is not known can be designated by (+) or (−)

depending on the direction in which they rotate plane polarized light. For instance, resolved enantiomers whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other stereoisomers. Thus, when a compound of Formula (I) is for instance specified as (R), this means that the compound is substantially free of the (S) isomer; when a compound of Formula (I) is for instance specified as E, this means that the compound is substantially free of the Z isomer; when a compound of Formula (I) is for instance specified as cis, this means that the compound is substantially free of the trans isomer.

Some of the compounds according to Formula (I) may also exist in their tautomeric form. Such forms in so far as they may exist, although not explicitly indicated in the above Formula (I) are intended to be included within the scope of the present invention.

It follows that a single compound may exist in both stereoisomeric and tautomeric form.

For therapeutic use, salts of the compounds of Formula (I) and solvates thereof, are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) and solvates thereof, are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) and solvates thereof containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of Formula (I) are able to form, as well as the pharmaceutically acceptable salts thereof. Examples of such forms are e.g. hydrates, alcoholates and the like.

The compounds of the invention as prepared in the processes described below may be synthesized in the form of mixtures of enantiomers, in particular racemic mixtures of enantiomers, that can be separated from one another following art-known resolution procedures. An manner of separating the enantiomeric forms of the compounds of Formula (I) and the pharmaceutically acceptable addition salts, and the solvates thereof, involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

As used in the specification and the appended claims, the singular forms "a", "an," and "the" also include plural referents unless the context clearly dictates otherwise. For example, "a compound" means 1 compound or more than 1 compound.

In an embodiment, the present invention concerns novel compounds of Formula
(I):

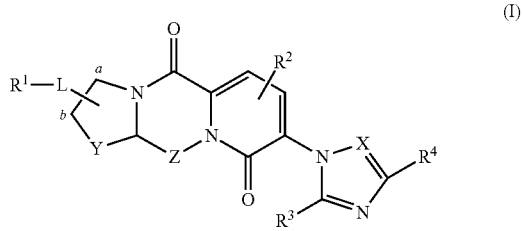

tautomers and stereoisomeric forms thereof, wherein
$R^1$ is phenyl, naphthyl, indolyl, benzothienyl, benzothiazolyl or benzofuranyl;
  each optionally substituted with one, two or three substituents each independently selected from the group consisting of halo and $C_{1-4}$alkyl optionally substituted with one, two or three halo substituents;
L is attached at position a or b;
  L is selected from the group consisting of a covalent bond, —$C_{1-6}$alkanediyl- and —O—$C_{1-6}$alkanediyl-;
Y is —$(CH_2)_n$— wherein one —$CH_2$— may be substituted with hydroxyl and $C_{1-4}$alkyl, -Q-$(CH_2)_m$— or —$CH_2$-Q-$CH_2$—;

n represents 1, 2 or 3;
m represents 1 or 2;
Q is O or $NR^6$;
$R^6$ is hydrogen or $C_{1-4}$alkyl;
Z is methylene or 1,2-ethanediyl, wherein methylene or 1,2-ethanediyl is optionally substituted with one or two $C_{1-4}$alkyl substituents;
$R^2$ is hydrogen, halo or $C_{1-4}$alkyl;
$R^3$ is hydrogen or $C_{1-4}$alkyl;
$R^4$ is hydrogen, halo or $C_{1-4}$alkyl;
X is $CR^5$ or N;
$R^5$ is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein:
$R^1$ is phenyl, napthyl or indolyl;
  each optionally substituted with one, two or three substituents each independently selected from the group consisting of halo and $C_{1-4}$alkyl optionally substituted with one, two or three halo substituents;
L is attached at position a;
  L is selected from the group consisting of a covalent bond, —$C_{1-6}$alkanediyl- and —O—$C_{1-6}$alkanediyl-;
Y is -Q-$(CH_2)_m$—, —$CH_2$-Q-$CH_2$—, —$(CH_2)_n$—,
  —$(CH_2)_n$— wherein one —$CH_2$— is substituted with hydroxyl and $C_{1-4}$alkyl, or
  —$(CH_2)_n$— wherein one —$CH_2$— is substituted with one hydroxyl;
n represents 1, 2 or 3;
m represents 1 or 2;
Q is O or $NR^6$;
$R^6$ is hydrogen or $C_{1-4}$alkyl;
Z is methylene;
$R^2$ is hydrogen;
$R^3$ is hydrogen or $C_{1-4}$alkyl;
$R^4$ is hydrogen, halo or $C_{1-4}$alkyl;
X is CH;
and the pharmaceutically acceptable addition salts, and the solvates thereof.

In an embodiment, the present invention concerns novel compounds of Formula (I), tautomers and stereoisomeric forms thereof, wherein:
$R^1$ is phenyl, napthyl, indolyl, benzothienyl, benzothiazolyl or benzofuranyl;
  each substituted with one, two or three substituents each independently selected from the group consisting of halo and $C_{1-4}$alkyl optionally substituted with one, two or three halo substituents;
L is attached at position a or b;
  L is selected from the group consisting of a covalent bond, —$C_{1-6}$alkanediyl- and —O—$C_{1-6}$alkanediyl-;
Y is -Q-$(CH_2)_m$—, —$CH_2$-Q-$CH_2$—, —$(CH_2)_n$—,
  —$(CH_2)_n$— wherein one —$CH_2$— is substituted with hydroxyl and $C_{1-4}$alkyl, or
  —$(CH_2)_n$— wherein one —$CH_2$— is substituted with one hydroxyl;
n represents 1, 2 or 3;
m represents 1 or 2;
Q is O or $NR^6$;
$R^6$ is hydrogen or $C_{1-4}$alkyl;
Z is methylene or 1,2-ethanediyl, wherein methylene or 1,2-ethanediyl is optionally substituted with one or two $C_{1-4}$alkyl substituents;
$R^2$ is hydrogen, halo or $C_{1-4}$alkyl;
$R^3$ is hydrogen or $C_{1-4}$alkyl;
$R^4$ is hydrogen, halo or $C_{1-4}$alkyl;
X is $CR^5$ or N;
$R^5$ is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^1$ is phenyl optionally substituted with one, two or three substituents each independently selected from the group consisting of halo and $C_{1-4}$alkyl optionally substituted with one, two or three halo substituents;
L is attached at position a; L is a covalent bond or $C_{1-6}$alkanediyl;
Y is —$(CH_2)_n$—,
n represents 1, 2 or 3;
Z is methylene or 1,2-ethanediyl, wherein methylene or 1,2-ethanediyl is optionally substituted with one or two $C_{1-4}$alkyl substituents;
$R^2$ is hydrogen, halo or $C_{1-4}$alkyl;
$R^3$ is hydrogen or $C_{1-4}$alkyl;
$R^4$ is hydrogen, halo or $C_{1-4}$alkyl;
X is $CR^5$ or N;
$R^5$ is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^1$ is phenyl optionally substituted with one, two or three substituents each independently selected from the group consisting of halo and $C_{1-4}$alkyl optionally substituted with one, two or three halo substituents;
L is attached at position a or b;
  L is selected from the group consisting of a covalent bond, —$C_{1-6}$alkanediyl- and —O—$C_{1-6}$alkanediyl-;
Y is -Q-$(CH_2)_m$—, —$CH_2$-Q-$CH_2$—, —$(CH_2)_n$—,
  —$(CH_2)_n$— wherein one —$CH_2$— is substituted with hydroxyl and $C_{1-4}$alkyl, or
  —$(CH_2)_n$— wherein one —$CH_2$— is substituted with one hydroxyl;
n represents 1, 2 or 3;
m represents 1 or 2;
Q is O or $NR^6$;
$R^6$ is hydrogen or $C_{1-4}$alkyl;
Z is methylene or 1,2-ethanediyl, wherein methylene or 1,2-ethanediyl is optionally substituted with one or two $C_{1-4}$alkyl substituents;
$R^2$ is hydrogen, halo or $C_{1-4}$alkyl;
$R^3$ is hydrogen or $C_{1-4}$alkyl;
$R^4$ is hydrogen, halo or $C_{1-4}$alkyl;
X is $CR^5$ or N;
$R^5$ is hydrogen or $C_{1-4}$alkyl;
and the pharmaceutically acceptable addition salts, and the solvates thereof.

In an embodiment, the present invention concerns novel compounds of Formula (I), tautomers and stereoisomeric forms thereof, wherein
$R^1$ is phenyl substituted with two substituents each independently selected from the group consisting of halo and $C_{1-4}$alkyl optionally substituted with three halo substituents;
L is attached at position a;
  L is selected from the group consisting of a covalent bond and —$C_{1-6}$alkanediyl-;
Y is —$(CH_2)_n$—;
n represents 1 or 2;

Z is methylene;
$R^2$ is hydrogen;
$R^3$ is hydrogen;
$R^4$ is $C_{1-4}$alkyl;
X is $CR^5$;
$R^5$ is hydrogen;
and the pharmaceutically acceptable addition salts, and the solvates thereof.

In an embodiment, the present invention concerns novel compounds of Formula (I), tautomers and stereoisomeric forms thereof, wherein
$R^1$ is phenyl substituted with two $CF_3$ substituents or two Cl substituents;
L is attached at position a;
  L is selected from the group consisting of a covalent bond and methylene;
Y is $-(CH_2)_n-$;
n represents 1 or 2;
Z is methylene;
$R^2$ is hydrogen;
$R^3$ is hydrogen;
$R^4$ is methyl;
X is $CR^5$;
$R^5$ is hydrogen;
and the pharmaceutically acceptable addition salts, and the solvates thereof.

In an embodiment, the present invention relates to those compounds of formula (I) and the pharmaceutically acceptable addition salts, and the solvates thereof, or any subgroup thereof as mentioned in any of the other embodiments, wherein $R^1$ is phenyl substituted with one, two or three substituents each independently selected from the group consisting of halo and $C_{1-4}$alkyl substituted with one, two or three halo substituents;
in particular $R^1$ is phenyl substituted with two substituents each independently selected from the group consisting of halo and $C_{1-4}$alkyl substituted with three halo substituents; more in particular $R^1$ is 3,5-bis(trifluoromethyl)-phenyl or 3,4-dichlorophenyl.

In an embodiment, the present invention relates to those compounds of formula (I) and the pharmaceutically acceptable addition salts, and the solvates thereof, or any subgroup thereof as mentioned in any of the other embodiments, wherein n is 1 or 2.

In an embodiment, the present invention relates to those compounds of formula (I) and the pharmaceutically acceptable addition salts, and the solvates thereof, or any subgroup thereof as mentioned in any of the other embodiments, wherein L is a covalent bond or methylene.

In an embodiment, the present invention relates to those compounds of formula (I) and the pharmaceutically acceptable addition salts, and the solvates thereof, or any subgroup thereof as mentioned in any of the other embodiments, wherein L is a covalent bond or $-C_{1-6}$alkanediyl-.

In an embodiment, the present invention relates to those compounds of formula (I) and the pharmaceutically acceptable addition salts, and the solvates thereof, or any subgroup thereof as mentioned in any of the other embodiments, wherein $R^1$ is phenyl, naphthyl or indolyl; each substituted with one, two or three substituents each independently selected from the group consisting of halo and $C_{1-4}$alkyl optionally substituted with one, two or three halo substituents.

In an embodiment, the present invention relates to those compounds of formula (I) and the pharmaceutically acceptable addition salts, and the solvates thereof, or any subgroup thereof as mentioned in any of the other embodiments, wherein Z is methylene.

In an embodiment, the present invention relates to those compounds of formula (I) and the pharmaceutically acceptable addition salts, and the solvates thereof, or any subgroup thereof as mentioned in any of the other embodiments, wherein $R^2$ is hydrogen.

In an embodiment, the present invention relates to those compounds of formula (I) and the pharmaceutically acceptable addition salts, and the solvates thereof, or any subgroup thereof as mentioned in any of the other embodiments, wherein $R^2$ is H.

In an embodiment, the present invention relates to those compounds of formula (I) and the pharmaceutically acceptable addition salts, and the solvates thereof, or any subgroup thereof as mentioned in any of the other embodiments, wherein $R^3$ is H.

In an embodiment, the present invention relates to those compounds of formula (I) and the pharmaceutically acceptable addition salts, and the solvates thereof, or any subgroup thereof as mentioned in any of the other embodiments, wherein $R^4$ is $C_{1-4}$alkyl or halo; in particular $C_{1-4}$alkyl; more in particular methyl.

In an embodiment, the present invention relates to those compounds of formula (I) and the pharmaceutically acceptable addition salts, and the solvates thereof, or any subgroup thereof as mentioned in any of the other embodiments, wherein L is attached at position a.

In an embodiment, the present invention relates to those compounds of formula (I) and the pharmaceutically acceptable addition salts, and the solvates thereof, or any subgroup thereof as mentioned in any of the other embodiments, wherein X is $CR^5$.

In an embodiment, the present invention relates to those compounds of formula (I) and the pharmaceutically acceptable addition salts, and the solvates thereof, or any subgroup thereof as mentioned in any of the other embodiments, wherein $R^5$ is H.

In an embodiment, the present invention relates to those compounds of formula (I) and the pharmaceutically acceptable addition salts, and the solvates thereof, or any subgroup thereof as mentioned in any of the other embodiments, wherein X is CH.

In an embodiment, the present invention relates to those compounds of formula (I) and the pharmaceutically acceptable addition salts, and the solvates thereof, or any subgroup thereof as mentioned in any of the other embodiments, wherein L is attached at position a or b; and L is selected from the group consisting of a covalent bond, $-CH_2-$ or $-O-CH_2-$.

In an embodiment, the present invention relates to those compounds of formula (I) and the pharmaceutically acceptable addition salts, and the solvates thereof, or any subgroup thereof as mentioned in any of the other embodiments, wherein L is attached at position a; and L is selected from the group consisting of a covalent bond, $-CH_2-$ or $-O-CH_2-$.

In an embodiment, the present invention relates to those compounds of formula (I) and the pharmaceutically acceptable addition salts, and the solvates thereof, or any subgroup thereof as mentioned in any of the other embodiments, wherein $R^1$ is phenyl, indolyl or naphthyl; in particular wherein $R^1$ is phenyl or indolyl; more in particular wherein $R^1$ is indolyl;

whereby phenyl, indolyl or naphthyl is (optionally) substituted according to any of the other embodiments.

In an embodiment the compound of Formula (I) is selected from the group consisting of:
3-(3,4-dichlorophenyl)-2,3,11,11a-tetrahydro-8-(4-methyl-1H-imidazol-1-yl)-1H-pyrido[1,2-a]pyrrolo[1,2-d]pyrazine-5,9-dione,
(3R,11aR)-3-(3,4-dichlorophenyl)-2,3,11,11a-tetrahydro-8-(4-methyl-1H-imidazol-1-yl)-1H-pyrido[1,2-a]pyrrolo[1,2-d]pyrazine-5,9-dione,
(3S,11aR)-3-(3,4-dichlorophenyl)-2,3,11,11a-tetrahydro-8-(4-methyl-1H-imidazol-1-yl)-1H-pyrido[1,2-a]pyrrolo[1,2-d]pyrazine-5,9-dione,
10-[3,5-bis(trifluoromethyl)phenyl]-6,6a,7,8,9,10-hexahydro-3-(4-methyl-1H-imidazol-1-yl)-dipyrido[1,2-a:1',2'-d]pyrazine-4,12-dione,
10-[3,5-bis(trifluoromethyl)phenyl]-6,6a,7,8,9,10-hexahydro-3-(4-methyl-1H-imidazol-1-yl)-dipyrido[1,2-a:1',2'-d]pyrazine-4,12-dione ((6aR, 10S) or (6aS, 10R)),
10-[3,5-bis(trifluoromethyl)phenyl]-6,6a,7,8,9,10-hexahydro-3-(4-methyl-1H-imidazol-1-yl)-dipyrido[1,2-a:1',2'-d]pyrazine-4,12-dione ((6aS, 10R) or (6aR, 10S),
3-[3,5-bis(trifluoromethyl)phenyl]-2,3,11,11a-tetrahydro-8-(4-methyl-1H-imidazol-1-yl)-1H-pyrido[1,2-a]pyrrolo[1,2-d]pyrazine-5,9-dione,
(3R,11aR)-3-[3,5-bis(trifluoromethyl)phenyl]-2,3,11,11a-tetrahydro-8-(4-methyl-1H-imidazol-1-yl)-1H-pyrido[1,2-a]pyrrolo[1,2-d]pyrazine-5,9-dione,
(3S,11aR)-3-[3,5-bis(trifluoromethyl)phenyl]-2,3,11,11a-tetrahydro-8-(4-methyl-1H-imidazol-1-yl)-1H-pyrido[1,2-a]pyrrolo[1,2-d]pyrazine-5,9-dione,
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione,
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione ((3R, 11aR) or (3S, 11aS)),
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione ((3S, 11aR) or (3R, 11aS)),
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione ((3S, 11aS) or (3R, 11aR)),
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione ((3R, 11aS) or (3S, 11aR)),
(3R,11aS)-3-[3,5-bis(trifluoromethyl)phenyl]-2,3,11,11a-tetrahydro-8-(4-methyl-1H-imidazol-1-yl)-1H-pyrido[1,2-a]pyrrolo[1,2-d]pyrazine-5,9-dione,
(3S,11aS)-3-[3,5-bis(trifluoromethyl)phenyl]-2,3,11,11a-tetrahydro-8-(4-methyl-1H-imidazol-1-yl)-1H-pyrido[1,2-a]pyrrolo[1,2-d]pyrazine-5,9-dione,
10-[[3,5-bis(trifluoromethyl)phenyl]methyl]-6,6a,7,8,9,10-hexahydro-3-(4-methyl-1H-imidazol-1-yl)-dipyrido[1,2-a:1',2'-d]pyrazine-4,12-dione,
10-[[3,5-bis(trifluoromethyl)phenyl]methyl]-6,6a,7,8,9,10-hexahydro-3-(4-methyl-1H-imidazol-1-yl)-dipyrido[1,2-a:1',2'-d]pyrazine-4,12-dione ((6aR, 10R) or (6aS, 10S)),
10-[[3,5-bis(trifluoromethyl)phenyl]methyl]-6,6a,7,8,9,10-hexahydro-3-(4-methyl-1H-imidazol-1-yl)-dipyrido[1,2-a:1',2-d]pyrazine-4,12-dione ((6aS, 10R) or (6aR, 10S)),
10-[[3,5-bis(trifluoromethyl)phenyl]methyl]-6,6a,7,8,9,10-hexahydro-3-(4-methyl-1H-imidazol-1-yl)-dipyrido[1,2-a:1',2-d]pyrazine-4,12-dione ((6aR, 10S) or (6aS, 10R)),
10-[[3,5-bis(trifluoromethyl)phenyl]methyl]-6,6a,7,8,9,10-hexahydro-3-(4-methyl-1H-imidazol-1-yl)-dipyrido[1,2-a:1',2-d]pyrazine-4,12-dione ((6aS, 10S) or (6aR, 10R)),
tautomers and stereoisomeric forms thereof,
and the pharmaceutically acceptable addition salts, and the solvates thereof.

In an embodiment the compound of Formula (I) is
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione,
tautomers and stereoisomeric forms thereof,
and the pharmaceutically acceptable addition salts, and the solvates thereof.

All possible combinations of the above-indicated interesting embodiments are considered to be embraced within the scope of this invention.

Preparation of the Compounds

The present invention also encompasses processes for the preparation of compounds of Formula (I), intermediates and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder and as described in the specific examples. They are generally prepared from starting materials which are either commercially available or prepared by standard means obvious to those skilled in the art. The compounds of the present invention can be also prepared using standard synthetic processes commonly used by those skilled in the art of organic chemistry.

The skilled person will realize that in some reactions microwave heating may be used instead of conventional heating to shorten the overall reaction time.

The general preparation of some typical examples is shown below.

Scheme 1

Experimental procedures-Scheme 1

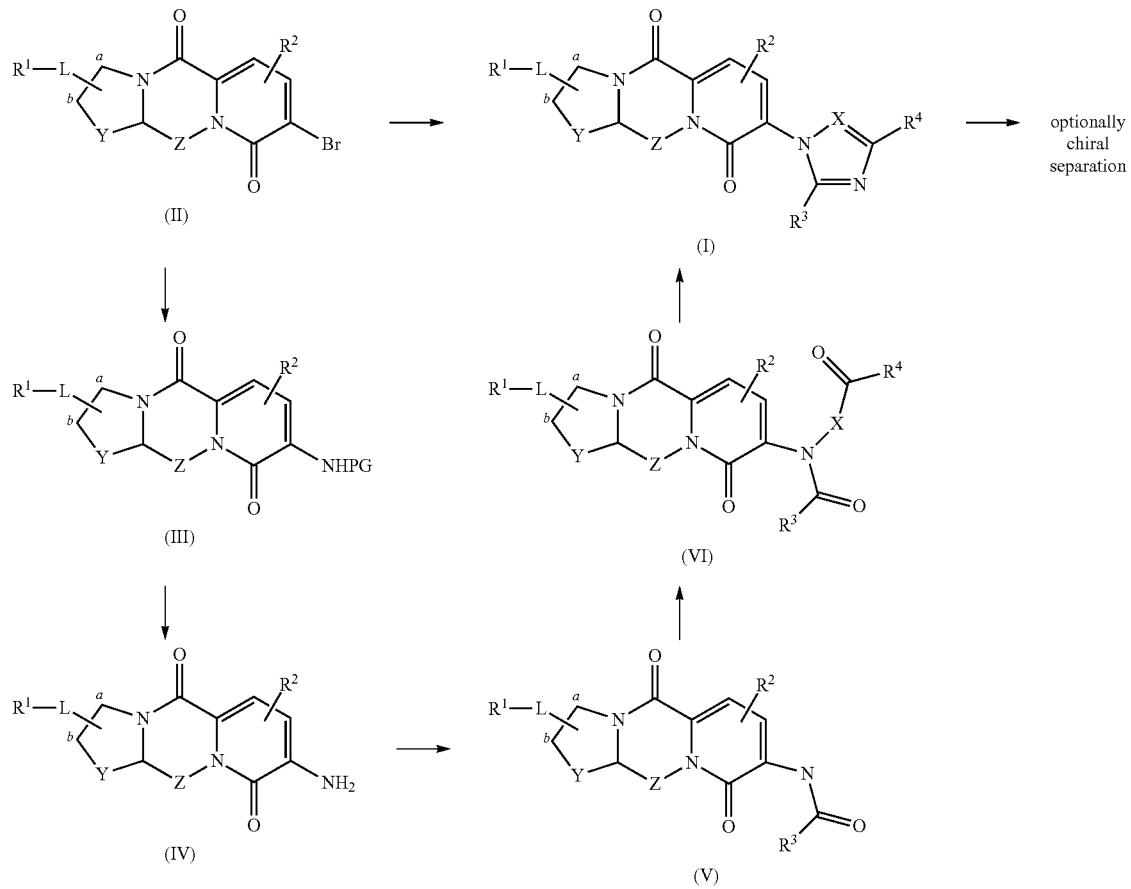

Experimental Procedure 1

A compound of formula (I), wherein all the variables are defined as described in the scope of the invention, can be obtained for example by copper catalyzed C—N coupling. Standard conditions involve stirring of intermediate (II) in the presence of a copper catalyst, such as CuI (copper iodide), a base, such as $Cs_2CO_3$ (cesium carbonate), the coupling partner, such as for example 4-methylimidazole, and a ligand, such as N,N'-dimethyl-1,2-cyclohexanediamine, in a suitable solvent, such as DMF (N,N-dimethyl formamide). Degassing the reaction mixture with an inert gas, such as $N_2$ or argon, and heating the reaction mixture to high temperatures, such as reflux temperature, may enhance the reaction outcome.

Alternatively, a compound of formula (I), where $R^3$ is restricted to hydrogen, can be obtained by palladium catalyzed C—N coupling. Typically, an intermediate of formula (II) is stirred and heated in the presence of a base, such as $K_3PO_4$ (potassium phosphate), a palladium source, such as $Pd_2(dba)_3$ (tris(dibenzylideneacetone)dipalladium(0)), a ligand, such as 2-di-tert-butylphosphino-3,4,5,6-tetramethyl-2',4',6'-triisopropyl-1,1'-biphenyl and the desired imidazole, in the presence of a solvent or a mixture of solvents, such as toluene/dioxane. Premixing of the catalyst and the ligand followed by heating before addition of the remaining reagents, degassing of the solution and heating can enhance the reaction outcome.

Alternatively, a compound of formula (I) wherein X is restricted to $CR^5$ and all the other variable are defined as described in the scope of the invention can be obtained via a 5-step synthesis.

In the first step, intermediate (II) can be converted into intermediate (III), where PG is a mono or divalent nitrogen protecting group. For example, when PG=acetyl, the reaction can be performed using known amide coupling methodologies. For example, acetamide can be reacted with intermediate (II) in the presence of a base, such as $K_3PO_4$, a palladium source, such as $Pd_2(dba)_3$, a ligand, such as (9,9-dimethyl-9H-xanthene-4,5-diyl)bis[diphenylphosphine](Xantphos), in a suitable solvent, such as dry THF (tetrahydrofuran). Degassing of the reaction mixture during the set-up with an inert gas, such as $N_2$ or argon, anhydrous conditions, and the use of high temperatures, such as reflux temperature, can enhance the reaction outcome. In the second step, intermediate (III) can be converted into the free amine intermediate (IV) by using any deprotection method tolerated by the other functionalities present in the molecule. For example, when PG in intermediate (III)=acetyl, an acidic hydrolysis, using for example HCl (hydrochloric acid), in a suitable solvent, such as MeOH (methanol), can be used. In the third step, the amino group in intermediate (IV) can be acylated to give intermediate (V). For example, if $R^3$ in compound (V) represents hydrogen, formylation of intermediate (IV) can be obtained by adding to intermediate (IV), dissolved in a suitable inert solvent, such as THF, a formylating agent, such as a mixture of acetic anhydride and formic acid. Stirring of the reaction under heating can enhance the reaction outcome. In the fourth step, intermediate (V) can be converted to the cyclization precursor (VI) with methodologies known to the person skilled in the art and depending on the desired functionalities X and $R^4$. For example, if in compound (VII) X=CH and $R^4$=alkyl, the reaction can be performed by adding the desired α-haloketone, such as for example 1-bromo-2-butanone, to a mixture of intermediate (V), and a base, such as $K_2CO_3$ (potassium carbonate), in a suitable solvent, such as DMF. If the halogen of the α-haloketone is different from iodine, the reaction can be improved by means of an in-situ Filkenstein reaction, performed by adding an iodine salt, such as KI, to the reaction mixture. Finally, intermediate (VII) can be converted into compound (I) by means of a classical imidazole synthesis. Diketo precursor (VII) can be cyclized into desired compound (I) in the presence of a nitrogen source, such as ammonium acetate, and an acid, such as AcOH. Heating the reaction to reflux temperature can enhance the reaction outcome.

can be used. For example, the reaction can be performed by dissolving intermediate (VII) in a mixture of solvents such as DCM (dichloromethane)/AcOH (acetic acid) and adding bromine to the mixture, or by adding NBS (N-bromosuccinimide) to a solution of intermediate (VII) in an appropriate solvent, such as acetonitrile. The reaction mixture may be stirred under heating and inert atmosphere.

Alternatively, an intermediate (II) can be obtained by intermolecular cyclization between an intermediate of formula (VIII), where $R^7$ is $C_{1-4}$alkyl and an intermediate of formula (X). Typical conditions involve stirring the ester in the presence of a desired aminoalcohol of formula (X) at high temperature.

Alternatively, starting as well from intermediate (VIII), intermediate (II) can be obtained by using a 2-step method. First, ester (VIII) can be saponified to give intermediate (IX), where M is a metal. The reaction can be performed for example by adding a hydroxide, such as LiOH (lithium hydroxide), to a solution of ester (VIII) in a suitable polar solvent or in a mixture of miscible solvents of which one is highly polar, such as THF and water. Heating the reaction mixture can enhance the reaction outcome. In the second step, intermediate (IX) can be reacted with an aminoalcohol of formula (X), to afford intermediate (II). Typically, peptide coupling conditions can be applied, such as stirring the starting material, dissolved in a suitable solvent, such as DMF, in the presence of a peptide coupling agent, such as HBTU (1-[bis(dimethylamino)methylene]-1H-benzotriazol- Scheme 2

Experimental procedures-Scheme 2

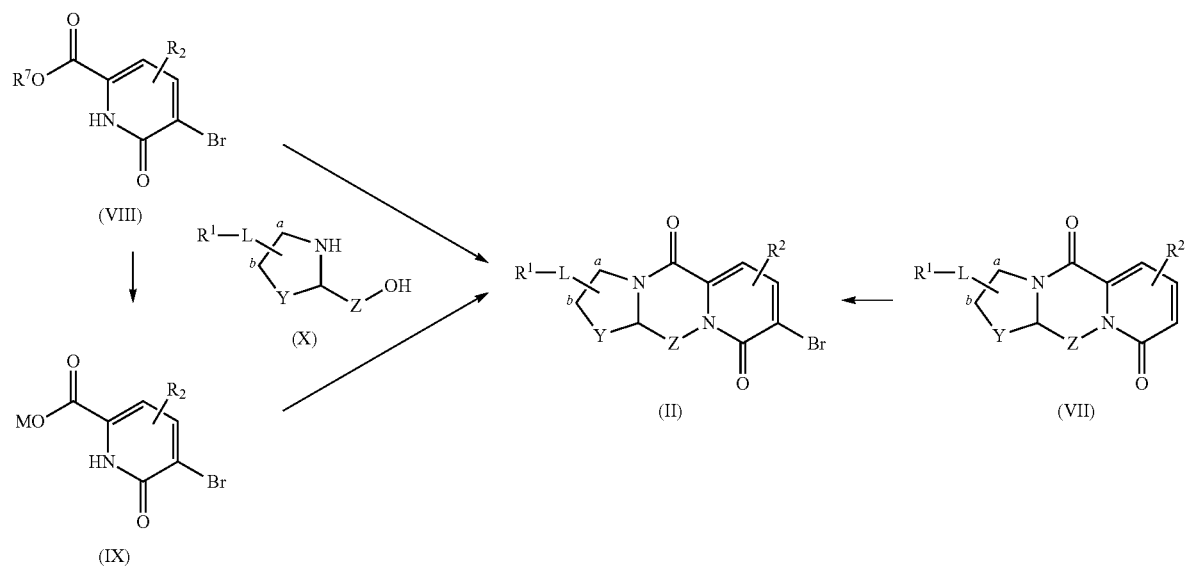

Experimental Procedure 2

An intermediate of formula (II), wherein all variables are defined as described in the scope of the invention, can be obtained starting from an intermediate of formula (VII) by means of direct bromination. Different brominating agents 1-ium 3-oxide hexafluorophosphate). The person skilled in the art will appreciate that when a base, such as DIPEA (N,N-diisopropylethylamine), is present in the mixture, the reaction affords directly the cyclized intermediate (II). Heating the reaction mixture can enhance the reaction outcome.

Scheme 2a

Experimental procedures-Scheme 2a

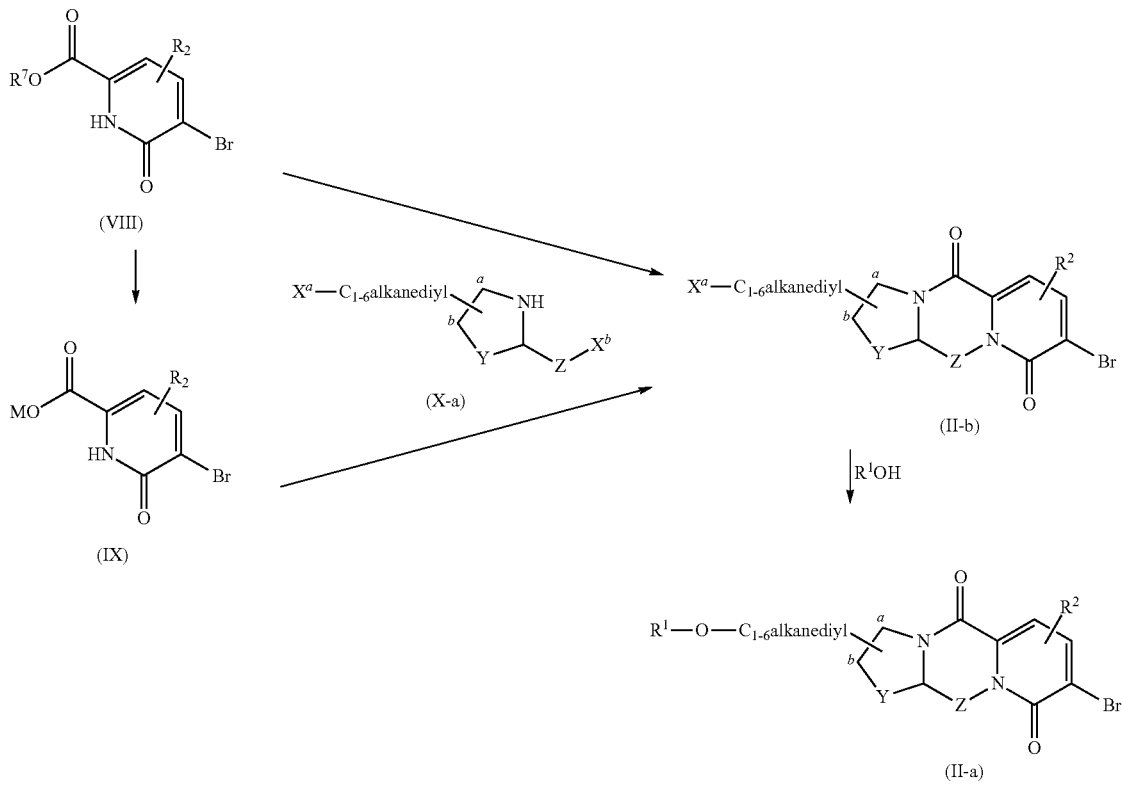

Experimental Procedure 3

An intermediate of formula (II), wherein L is —O—C$_{1-6}$alkanediyl-; and all variables are defined as described in the scope of the invention, hereby named (II-a) can be obtained by nucleophilic substitution of an intermediate of formula (II-b) with an alcohol of formula R$^1$OH wherein R$^1$ is defined as described in the scope of the invention. The reaction mixture may be stirred in presence of a suitable base such as K$_2$CO$_3$ in as solvent such as DMF under heating and inert atmosphere.

Experimental Procedure 4

An intermediate of formula (II-b), wherein
X$^a$ is Cl, Br, I, OH, OMs (mesylate), OTs (tosylate);
and all the other variables are defined as described in the scope of the invention, can be obtained by intermolecular cyclization between an intermediate of formula (VIII), where R$^7$ is C$_{1-4}$alkyl and an intermediate of formula (X-a) wherein X$^b$ is Cl, Br, I, OH, OMs, OTs. Typical conditions involve stirring the ester in the presence of a desired aminoalcohol of formula (X-a) at high temperature.

Alternatively, starting as well from intermediate (VIII), intermediate (II-b) can be obtained by using a 2-step method. First, ester (VIII) can be saponified to give intermediate (IX), where M is a metal. The reaction can be performed for example by adding a hydroxide, such as LiOH (lithium hydroxide), to a solution of ester (VIII) in a suitable polar solvent or in a mixture of miscible solvents of which one is highly polar, such as THF and water. Heating the reaction mixture can enhance the reaction outcome. In the second step, intermediate (IX) can be reacted with an aminoalcohol of formula (X-a), to afford intermediate (II-b). Typically, peptide coupling conditions can be applied, such as stirring the starting material, dissolved in a suitable solvent, such as DMF, in the presence of a peptide coupling agent, such as HBTU (1-[bis(dimethylamino)methylene]-1H-benzotriazol-1-ium 3-oxide hexafluorophosphate). The person skilled in the art will appreciate that when a base, such as DIPEA (N,N-diisopropylethylamine), is present in the mixture, the reaction affords directly the cyclized intermediate (II-b). Heating the reaction mixture can enhance the reaction outcome.

An intermediate of formula (X-a), wherein
X$^a$ is Cl, Br, I, OH, OMs, OTs;
X$^b$ is Cl, Br, I, OH, OMs, OTs;
and all the other variables are defined as described in the scope of the invention, can be obtained commercially or can be prepared starting from commercially available compounds by methods known to the person skilled in the art.

Scheme 3

Experimental procedures-Scheme 3

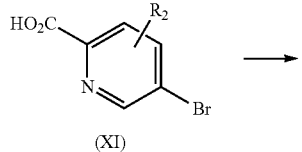

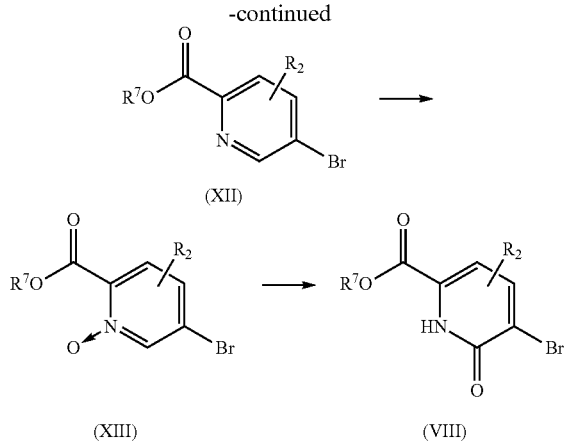

(XII)

(XIII)  (VIII)

Experimental Procedure 5

An intermediate of formula (VIII), wherein
$R^7$ is $C_{1-4}$alkyl;
and all the other variables are defined as described in the scope of the invention, is commercially available or can be obtained via acidic hydrolysis of intermediate (XIII). The reaction can be performed for example by stirring the starting materials in the presence of an acid, such as trifluoroacetic anhydride, in a suitable solvent, such as DMF. The reaction mixture may be stirred under heating and inert atmosphere.

Experimental Procedure 6

An intermediate of formula (XIII), wherein
$R^7$ is $C_{1-4}$alkyl;
and all the other variables are defined as described in the scope of the invention, can be obtained by N-oxydation of intermediate (XII), by methods known to the person skilled in the art. The reaction can be performed for example in the presence of a peroxide, such as urea hydrogen peroxide, and an activation agent, such as trifluoroacetic anhydride, in a suitable solvent, such as MeCN (acetonitrile).

Experimental Procedure 7

An intermediate of formula (XII), wherein
$R^7$ is $C_{1-4}$alkyl;
and all the other variables are defined as described in the scope of the invention, can be obtained by esterification of the commercially available intermediate (XI), by methods known to the person skilled in the art. The reaction can be performed for example in the presence of a chlorinating agent, such as thionyl chloride, and an alcohol, such as MeOH, in a suitable solvent, such as MeOH. Precooling of the solution before addition of the chlorinating agent can enhance the outcome of the reaction.

Scheme 4

Experimental procedures-Scheme 4

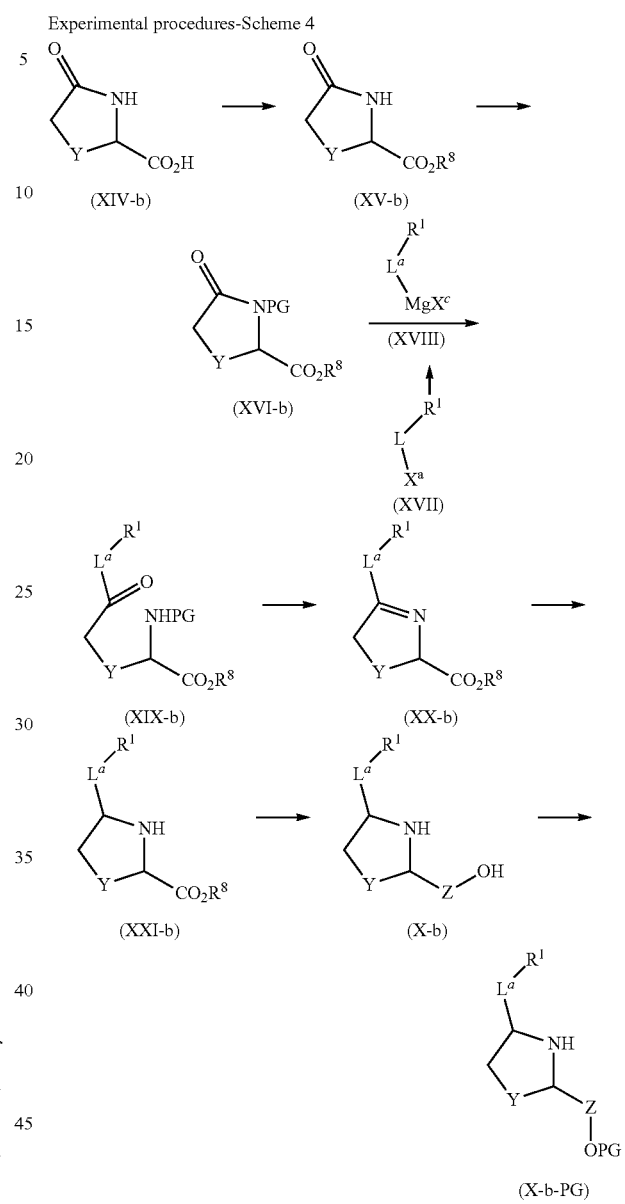

Experimental Procedure 8

An intermediate of formula (X-b-PG), wherein L is restricted to $L^a$
$L^a$ being attached at position a;
$L^a$ being a covalent bond or —$C_{1-6}$alkanediyl—;
PG is a protecting group known to those skilled in the art;
and all the other variables are defined as described in the scope of the invention, can be obtained via protection of the alcohol functionality of intermediate (X-b). The protection can be for example a silylation, that can be performed in the presence of a suitable solvent, such as DCM, an additive, such as imidazole, and a silylating agent, such as TBSCl (tert-butyldimethylsilyl chloride) or TMSCl (trimethylsilyl chloride), following standard conditions known to the person skilled in the art.

Experimental Procedure 9

An intermediate of formula (X-b), wherein all the variables are defined as described in the scope of the invention, can be obtained via reduction of the ester functionality of intermediate (XXI-b) for example by using NaBH$_4$ (sodium borohydride) or LiAlH$_4$ (lithium aluminium hydride) in the presence of a suitable solvent, such as MeOH or Et$_2$O (diethylether). Precooling of the reaction mixture before addition of the reducing agent, may enhance the reaction outcome.

Experimental Procedure 10

An intermediate of formula (XXI-b), wherein
R$^8$ is C$_{1-4}$alkyl;
and all the variables are defined as described in the scope of the invention, can be obtained via reduction of the imino functionality of intermediate (XX-b) for example by using NaBH$_3$CN (sodium cyanoborohydride) in the presence of a suitable solvent, such as 2-propanol. Precooling of the reaction mixture before addition of the reducing agent, may enhance the reaction outcome.

Experimental Procedure 11

An intermediate of formula (XX-b), wherein
R$^8$ is C$_{1-4}$alkyl;
and all the other variables are defined as described in the scope of the invention, can be obtained by means of deprotection methods known to the person skilled in the art followed by in-situ cyclization. For example, when PG=Boc (tert-butoxycarbonyl), deprotection can be achieved by treating intermediate (XIX-b), dissolved in a suitable solvent, such as DCM, with a strong acid, such as TFA (trifluoroacetic acid).

Experimental Procedure 12

An intermediate of formula (XVIII), wherein
X$^c$ is chlorine or bromine;
and all the other variables are defined as described in the scope of the invention, can be obtained commercially or by means of preparation of a Grignard reagent with intermediate of formula (XVII) following methods known to the person skilled in the art. Typical conditions would be for example treating intermediate (XVII) with magnesium in a suitable inert solvent, such as Et$_2$O. The reaction mixture may be stirred under heating and inert atmosphere.

Experimental Procedure 13

An intermediate of formula (XIX-b), wherein
R$^8$ is C$_{1-4}$alkyl and PG is a protecting group known to those skilled in the art;
and all the other variables are defined as described in the scope of the invention, can be obtained by reaction of an intermediate of formula (XVI-b) with an intermediate of formula (XVIII). Precooling of the solution before addition of the Grignard reagent can enhance the outcome of the reaction.

Experimental Procedure 14

An intermediate of formula (XVI-b), wherein
R$^8$ is C$_{1-4}$alkyl and PG is a protecting group known to those skilled in the art;
and all the other variables are defined as described in the scope of the invention, can be obtained via protection of the amide functionality of intermediate (XV-b). The protection can be for example a Boc protection that can be performed in the presence of a suitable solvent, such as MeCN, an additive, such as DMAP (dimethylaminopyridine), and the protecting agent, such as (Boc)$_2$O (di-tert-butyldicarbonate), following standard conditions known to the person skilled in the art.

Experimental Procedure 15

An intermediate of formula (XV-b), wherein
R$^8$ is C$_{1-4}$alkyl;
and all the other variables are defined as described in the scope of the invention, can be obtained by esterification of a commercially available intermediate (XIV-b), by methods known to the person skilled in the art. The reaction can be performed for example in the presence of a chlorinating agent, such as thionyl chloride, and an alcohol, such as EtOH, in a suitable solvent, such as EtOH. Precooling of the solution before addition of the chlorinating agent can enhance the outcome of the reaction.

Scheme 4a

Experimental procedures-Scheme 4a

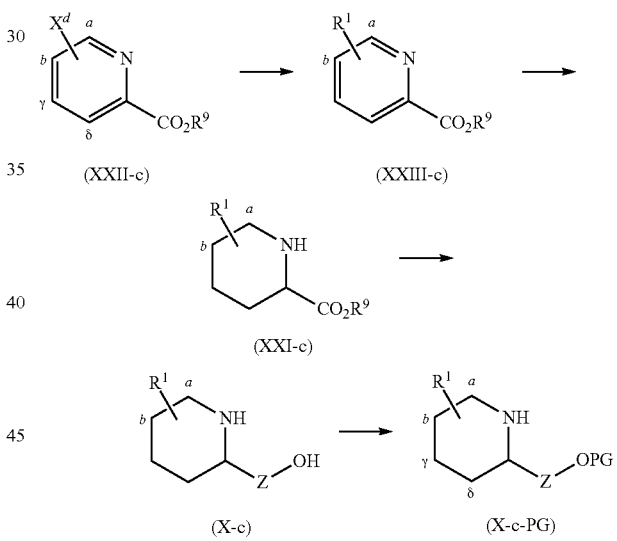

Alternatively, an intermediate of formula (X), wherein
L is attached at position a or b and restricted to a covalent bond;
Y is —(CH$_2$)— with n=2;
PG is a protecting group, hereby called intermediate (X-c-PG), may be obtained starting from intermediate (X-c) via protection of the alcohol functionality of intermediate (X-c). For example the protection can be a silylation, that can be performed in the presence of a suitable solvent, such as DCM, an additive, such as imidazole, and a silylating agent, such as TBSCl or TMSCl, following standard conditions known to the person skilled in the art.

Intermediate of formula (X-c) wherein all the variables are defined as described in the scope of the invention, can be obtained by reduction of the ester functionality of intermediate (XXI-c) for example by using NaBH$_4$ in the presence of a suitable solvent, such as MeOH. Precooling of the reaction mixture before addition of the reducing agent, may enhance the reaction outcome.

sponding intermediate containing a hydroxyl and $C_{1-4}$alkyl moiety on one $CH_2$ in position γ or δ.

Scheme 5

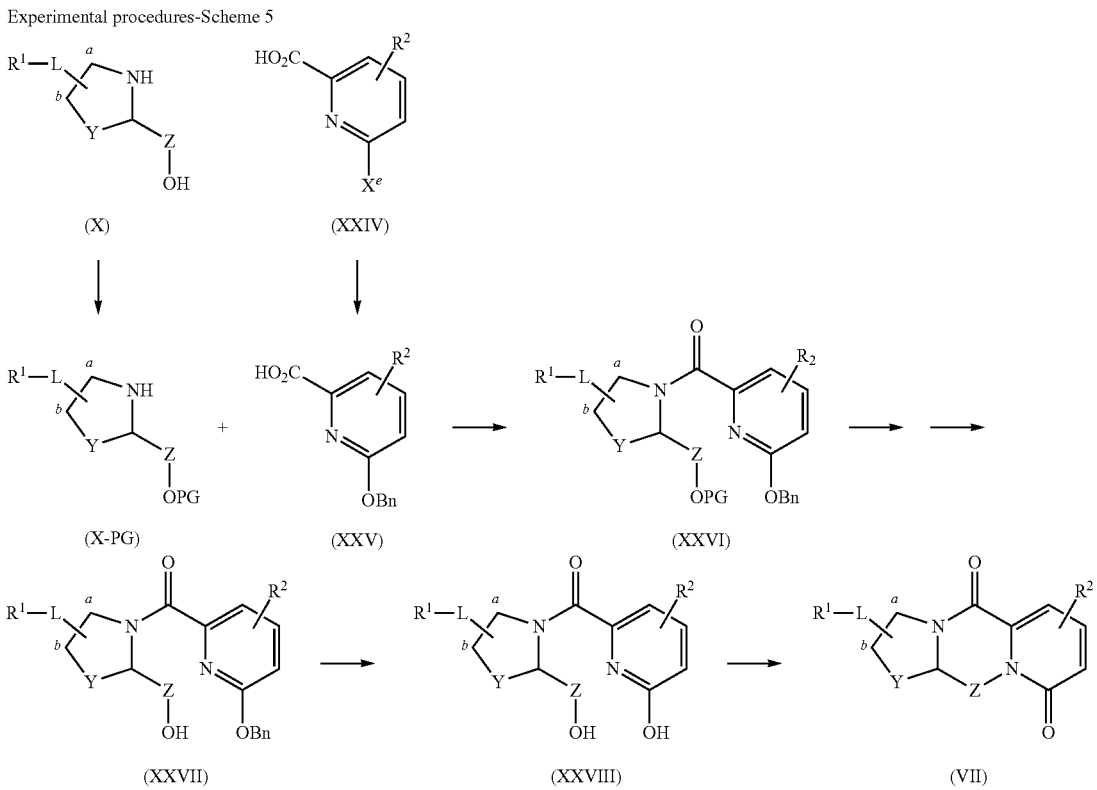

Intermediate of formula (XXI-c) wherein
$R^9$ is $C_{1-4}$alkyl;
and all the other variables are defined as described in the scope of the invention, can be obtained by hydrogenation of intermediate (XXIII-c) for example by stirring a solution of intermediate (XXIII-c) in a suitable solvent, such as AcOH (acetic acid), and in the presence of a hydrogenation catalyst, such as $PtO_2$ (platinum (IV) oxide), under hydrogen atmosphere.

Intermediate of formula (XXIII-c) wherein
$R^9$ is $C_{1-4}$alkyl;
and all the other variables are defined as described in the scope of the invention, can be obtained for example by palladium catalyzed C—C coupling. Standard conditions involve stirring of commercially available intermediate (XXII-c) (wherein $X^d$ is Br, Cl or I) in the presence of a palladium catalyst, such as tetrakis(triphenylphosphine)palladium(0), a suitable base, such as $K_2CO_3$ and the coupling partner, such as for example 3,5-bis(trifluoromethyl)phenylboronic acid and in a suitable solvent, such as DMF. Degassing the reaction mixture with an inert gas, such as $N_2$ or argon, and heating the reaction mixture to high temperatures, such as reflux temperature, may enhance the reaction outcome.

Optionally, an intermediate of formula (XXII-c) may be substituted with hydroxyl in position γ or δ. Said hydroxyl group may be oxidized in an intermediate of formula (XXI-c) to obtain the corresponding ketone, which subsequently may be converted with a Grignard reaction to the corre- Experimental Procedure 14

An intermediate of formula (VII) wherein all the variables are defined as described in the scope of the invention, can be obtained via intramolecular cyclization, for example by applying Mitsunobu conditions to intermediate (XXVIII). The reaction can be performed by treating a solution of intermediate (XXVIII) in a suitable inert and dry solvent, such as THF, with an azadicarboxylate species, such as DIAD (diisopropyl azodicarboxylate), in the presence of a phosphine, such as triphenylphosphine, under inert atmosphere. Precooling of the solution may be used.

Experimental Procedure 15

An intermediate of formula (XXVIII) can be obtained via debenzylation of a compound of formula (XXVII) using standard methods compatible with the presence of the protecting group. In the case of intermediate (XXVII), for example, debenzylation can be achieved by hydrogenation by stirring a solution of intermediate (XXVII) in a suitable solvent, such as MeOH, and in the presence of a hydrogenation catalyst, such as Pd/C (palladium on carbon), under hydrogen atmosphere.

Experimental Procedure 16

An intermediate of formula (XXVII) can be obtained by deprotection of intermediate (XXVI), by methods known to the person skilled in the art. In the case of a silyl protecting group, for example, one standard method would be treating intermediate (XXVI), dissolved in a suitable solvent, such as THF, with a fluoride source, such as TBAF (tetrabutylammonium fluoride).

Experimental Procedure 17

An intermediate of formula (XXVI) can be obtained by starting from intermediate (X-PG) and acid (XXV), using for example standard peptide coupling conditions. Typically, peptide coupling conditions can be applied, such as stirring the starting materials, dissolved in a suitable solvent, such as DMF, in the presence of a peptide coupling agent, such as HBTU and in the presence of a base, such as DIPEA. Cooling the reaction mixture can enhance the reaction outcome.

Experimental Procedure 18

An intermediate of formula (X-PG) can be obtained via protection of the alcohol functionality of intermediate (X). The protection can be for example a silylation, that can be performed in the presence of a suitable solvent, such as DCM, an additive, such as imidazole, and a silylating agent, such as TBSCl or TMSCl, following standard conditions known to the person skilled in the art.

Experimental Procedure 19

An intermediate of formula (XXV) can be obtained by protection of intermediate (XXIV), wherein $X^c$ is Cl, Br and I, compatible with the presence of the protecting group in the following step. The protection can be for example a benzylation, that can be performed in the presence of a suitable solvent, such as THF, a suitable base such as NaH (sodium hydride), and benzyl alcohol, following standard conditions known to the person skilled in the art.

Scheme 6

Experimental procedures-Scheme 6

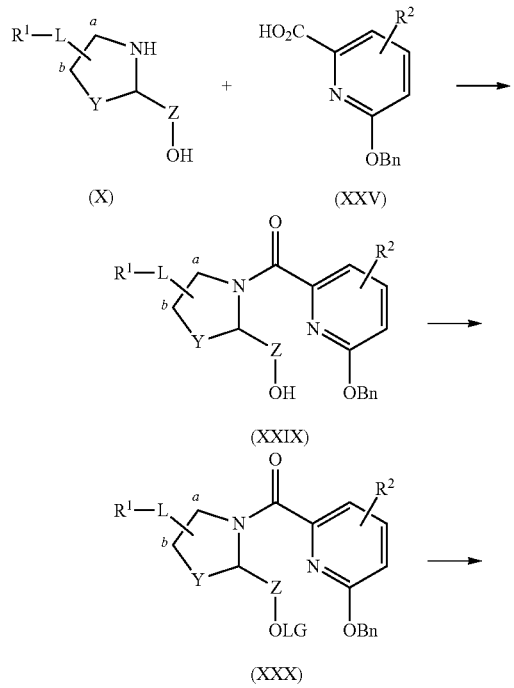

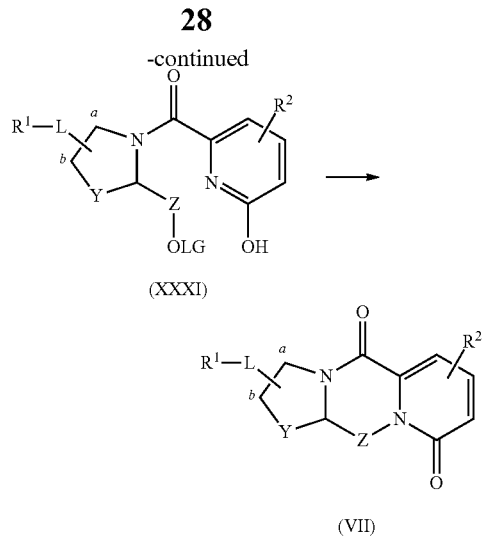

Experimental Procedure 20

Alternatively, starting from intermediate (X) and intermediate (XXV) a 4-step method can be used. First, typically, peptide coupling conditions can be applied, such as stirring the starting materials, dissolved in a suitable solvent, such as DMF, in the presence of a peptide coupling agent, such as HBTU and in the presence of a base, such as DIPEA. Cooling the reaction mixture can enhance the reaction outcome. Then, the free hydroxyl function in intermediate (XXIX) can be converted into a suitable leaving group. For example, intermediate (XXX), where LG=chlorine and where Bn=benzyl, can be obtained under mild conditions by dissolving intermediate (XXIX) in a suitable solvent, such as DCM, and treating it with a chlorinating agent, such as thionyl chloride. Precooling of the solution before addition of the chlorinating agent can enhance the outcome of the reaction. Intermediate (XXX) can then undergo debenzylation to give intermediate (XXXI), using standard methods compatible with the presence of the leaving group. For example, debenzylation can be achieved by treating the intermediate, dissolved in a suitable and inert solvent, such as DCM, with a Lewis acid such as BBr$_3$ (boron tribromide). Precooling of the reaction mixture before addition of the Lewis acid can enhance the reaction outcome. Finally, intermediate (XXXI) can be processed to intermediate (VII) by using standard substitution conditions. For example, starting from intermediate (XXXI), where LG=chlorine, the ring closure can be achieved by treating the substrate, dissolved in a suitable solvent, such as DMF, with a base, such as NaH. Precooling of the reaction and a level of dilution high enough to avoid intermolecular reactions can enhance the reaction outcome.

Starting materials can be obtained commercially or can be prepared by those skilled in the art.

Where necessary or desired, any one or more of the following further steps in any order may be performed:

Compounds of Formula (I) and any subgroup thereof may be converted into further compounds of Formula (I) and any subgroup thereof, using procedures known in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

In all these preparations, the reaction products may be isolated from the reaction medium and, if necessary, further purified according to methodologies generally known in the art such as, for example, extraction, crystallization, trituration and chromatography. In particular, stereoisomers can be isolated chromatographically using a chiral stationary phase such as, for example, Chiralpak® AD (amylose 3,5 dimethyl-phenyl carbamate) or Chiralpak® AS, both purchased from Daicel Chemical Industries, Ltd, in Japan, or by Supercritical Fluid Chromatography (SFC).

The chirally pure forms of the compounds of Formula (I) form a preferred group of compounds. It is therefore that the chirally pure forms of the intermediates and their salt forms are particularly useful in the preparation of chirally pure compounds of Formula (I). Also enantiomeric mixtures of the intermediates are useful in the preparation of compounds of Formula (I) with the corresponding configuration.

Pharmacology

It has been found that the compounds of the present invention modulate the γ-secretase activity. The compounds according to the invention and the pharmaceutically acceptable compositions thereof therefore may be useful in the treatment or prevention of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid; preferably AD.

The compounds according to the present invention and the pharmaceutically acceptable compositions thereof may be useful in the treatment or prevention of a disease or condition selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

A skilled person will be familiar with alternative nomenclatures, nosologies, and classification systems for the diseases or conditions referred to herein. For example, the fifth edition of the Diagnostic & Statistical Manual of Mental Disorders (DSM-5™) of the American Psychiatric Association utilizes terms such as neurocognitive disorders (NCDs) (both major and mild), in particular, neurocognitive disorders due to Alzheimer's disease, due to traumatic brain injury (TBI), due to Lewy body disease, due to Parkinson's disease or to vascular NCD (such as vascular NCD present with multiple infarctions). Such terms may be used as an alternative nomenclature for some of the diseases or conditions referred to herein by the skilled person.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, or an alleviation of symptoms, but does not necessarily indicate a total elimination of all symptoms.

The term "subject" as used herein, refers to an animal, preferably a mammal, most preferably a human, who is or has been the object of treatment, observation or experiment.

The invention relates to compounds according to the general Formula (I), and the pharmaceutically acceptable acid or base addition salts and the solvates thereof, for use as a medicament.

The invention also relates to compounds according to the general Formula (I), and the pharmaceutically acceptable acid or base addition salts and the solvates thereof, for use in the modulation of γ-secretase activity.

The invention also relates to compounds according to the general Formula (I), and the pharmaceutically acceptable acid or base addition salts and the solvates thereof, for use in the treatment or prevention of diseases or conditions selected from the group consisting of AD, TBI, dementia pugilistica, MCI, senility, dementia, dementia with Lewy bodies, cerebral amyloid angiopathy, multi-infarct dementia, Down's syndrome, dementia associated with Parkinson's disease and dementia associated with beta-amyloid.

The invention also relates to compounds according to the general Formula (I), and the pharmaceutically acceptable acid or base addition salts and the solvates thereof for use in the treatment or prevention of a disease or condition selected from neurocognitive disorder due to Alzheimer's disease, neurocognitive disorder due to traumatic brain injury, neurocognitive disorder due to Lewy body disease, neurocognitive disorder due to Parkinson's disease or vascular neurocognitive disorder.

In an embodiment, said disease or condition is preferably AD.

The invention also relates to compounds according to the general Formula (I), and the pharmaceutically acceptable acid or base addition salts and the solvates thereof, for use in the treatment of said diseases.

The invention also relates to compounds according to the general Formula (I), and the pharmaceutically acceptable acid or base addition salts and the solvates thereof, for the treatment or prevention of said diseases.

The invention also relates to compounds according to the general formula (I), and the pharmaceutically acceptable acid or base addition salts and the solvates thereof, for the treatment or prevention, in particular treatment, of γ-secretase mediated diseases or conditions.

The invention also relates to the use of compounds according to the general Formula (I), and the pharmaceutically acceptable acid or base addition salts and the solvates thereof, for the manufacture of a medicament.

The invention also relates to the use of compounds according to the general Formula (I), and the pharmaceutically acceptable acid or base addition salts and the solvates thereof, for the manufacture of a medicament for the modulation of γ-secretase activity.

The invention also relates to the use of compounds according to the general Formula (I), and the pharmaceutically acceptable acid or base addition salts and the solvates thereof, for the manufacture of a medicament for the treatment or prevention of any one of the disease conditions mentioned hereinbefore.

The invention also relates to the use of compounds according to the general Formula (I), and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), and the pharmaceutically acceptable acid or base addition salts and the solvates thereof, or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assay used in the Examples below.

The compounds of Formula (I), and the pharmaceutically acceptable acid or base addition salts and the solvates thereof, can be administered to mammals, preferably humans for the treatment or prevention of any one of the diseases mentioned hereinbefore.

In view of the utility of the compounds of Formula (I), and the pharmaceutically acceptable acid or base addition salts and the solvates thereof, there is provided a method of treating a subject, in particular warm-blooded animals, including humans, suffering from or a method of preventing a subject, in particular warm-blooded animals, including humans, suffering from any one of the diseases mentioned hereinbefore.

Said methods comprise the administration, i.e. the systemic or topical administration, preferably oral administration, of a therapeutically effective amount of a compound of Formula (I), and the pharmaceutically acceptable acid or base addition salts and the solvates thereof, to a subject, in particular warm-blooded animals, including humans.

Therefore, the invention also relates to a method of treating or preventing a disease or condition selected from Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid, comprising administering to a subject in need thereof, a therapeutically effective amount of a compound or a pharmaceutical composition according to the invention.

The invention also relates to a method of treating or preventing a disease or condition selected from neurocognitive disorder due to Alzheimer's disease, neurocognitive disorder due to traumatic brain injury, neurocognitive disorder due to Lewy body disease, neurocognitive disorder due to Parkinson's disease or vascular neurocognitive disorder, comprising administering to a subject in need thereof, a therapeutically effective amount of a compound or a pharmaceutical composition according to the invention.

The present invention also concerns to the use of compounds of Formula (I), and the pharmaceutically acceptable acid or base addition salts and the solvates thereof, for the modulation of γ-secretase activity resulting in a decrease in the relative amount of Aβ42-peptides produced.

An advantage of the compounds or a part of the compounds of the present invention may be their enhanced CNS-penetration.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I), a pharmaceutically acceptable acid or base addition salt, or a solvate thereof, and one or more additional therapeutic agents, as well as administration of the compound of Formula (I), a pharmaceutically acceptable acid or base addition salt, or a solvate thereof, and each additional therapeutic agents in its own separate pharmaceutical dosage formulation. For example, a compound of Formula (I), a pharmaceutically acceptable acid or base addition salt, or a solvate thereof, and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I), a pharmaceutically acceptable acid or base addition salt, or a solvate thereof.

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), and the pharmaceutically acceptable acid or base addition salts and the solvates thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing a compound of Formula (I), a pharmaceutically acceptable acid or base addition salt, or a solvate thereof, may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I), pharmaceutically acceptable acid or base addition salts and the solvates thereof, in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of Formula (I), a pharmaceutically acceptable acid or base addition salt, or a solvate thereof, and from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention. In case no specific stereochemistry is indicated for a stereocenter of a compound, this means that the compound was obtained as a mixture of the R and the S enantiomers.

EXAMPLES

Hereinafter, the term "AcOH" means acetic acid; "aq." means aqueous; "Bn" means benzyl; "DCM" means dichloromethane; "DIPE" means diisopropylether; "DIPEA" means N,N-diisopropylethylamine; "DMAP" means 4-(dimethylamino)pyridine; "DMF" means N,N-dimethylformamide; "DMSO" means dimethyl sulfoxide; "Et₃N" means triethylamine; "EtOH" means ethanol; Et₂O means diethylether; "EtOAc" means ethyl acetate; "h" means hour(s); "HBTU" means 1-[bis(dimethylamino)methylene]-1H-benzotriazol-1-ium 3-oxide hexafluorophosphate; "HPLC" means high-performance liquid chromatography; "LCMS" means Liquid Chromatography/Mass spectrometry; "MeCN" means acetonitrile; "MeOH" means methanol; "min" means minute(s); "m.p." means melting point; "Pd (PPh₃)₄" means tetrakis(triphenylphosphine)palladium; "Pd₂(dba)₃" means tris[μ-[(1,2-η:4,5-η)-(1E,4E)-1,5-diphenyl-1,4-pentadien-3-one]]dipalladium; "Pd(OAc)₂" means palladium(2+) diacetate; "r.m." means reaction mixture(s); "RP" means reversed phase; "r.t." means room temperature; "sat." means saturated; "sol." means solution; "TBDMS" means tertbutyldimethylsilyl; "TFA" means trifluoroacetic acid and "THF" means tetrahydrofuran.

A. Preparation of the Intermediates

Example A1

A) Preparation of Intermediate 1

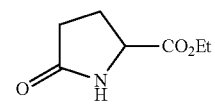 [SMILES: CCOC(=O)C1CCC(=O)N1]

A sol. of DL-pyroglutamic acid (90 g, 697 mmol) and 4-methylbenzenesulfonic acid hydrate (13.26 g, 69.7 mmol) in EtOH (110 ml) was stirred at 65° C. for 72 h. The r.m. was cooled to r.t. and evaporated in vacuo. Et$_2$O (1 l) was added and the mixture was washed with a sat. aq. NaHCO$_3$ sol. (300 ml). The separated organic phase was dried (MgSO$_4$), filtered. The aqueous phase was extracted with DCM (3 times). The separated organic phase was dried (MgSO$_4$), filtered and the organic layers combined and evaporated in vacuo. Yield: 80 g of intermediate 1 (73%).

B) Preparation of Intermediate 2

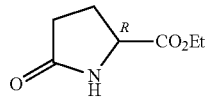

Thionyl chloride (5.45 ml, 74.76 mmol) was added dropwise to D-glutamic acid (5 g, 34 mmol) in EtOH (25 ml) at 5° C. over 1 h. After the addition was completed, the r.m. was stirred at r.t. for 1 h and then heated at 80° C. for 1 h. The r.m. was evaporated in vacuo. The residue was taken into EtOH and neutralized to pH 7 with a KOH 1% sol. in EtOH. The solid was filtered and the filtrate was concentrated to dryness. The residue was heated at 90° C. for 1 h and at 150° C. for 1 h under high vacuum (1 mmbar). The residue was washed with heptane and dried in vacuo. The crude material was used as such for the next reaction step. Yield: 3.92 g of intermediate 2 (73%).

Example A2

A) Preparation of Intermediate 3

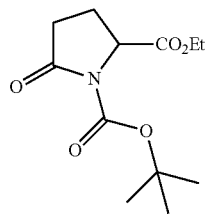 [SMILES: CCOC(=O)C1CCC(=O)N1C(=O)OC(C)(C)C]

A mixture of intermediate 1 (4.3 g, 27.36 mmol), di-tert-butyl dicarbonate (7.17 g, 32.83 mmol), DMAP (0.17 g, 1.37 mmol) in MeCN (43.6 ml) was stirred under nitrogen at r.t. for 2 h. The solvent was evaporated in vacuo and the residue was dissolved in Et$_2$O (200 ml). The organic phase was cooled to 0° C. and washed with a HCl 1N sol. (15 ml) and then brine (20 ml). The separated organic phase was dried (MgSO$_4$), filtered and the organic layers combined and evaporated in vacuo. The crude product was purified by flash column chromatography (eluent: EtOAc/DCM from 5/95 to 10/90). The product fractions were collected and the solvent evaporated in vacuo. Yield: 6.6 g of intermediate 3 (94%).

B) Preparation of Intermediate 4

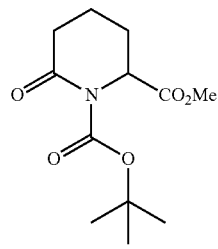 [SMILES: COC(=O)C1CCCC(=O)N1C(=O)OC(C)(C)C]

Starting from 6-oxo-piperidine-2-carboxylic acid methyl ester, intermediate 4 was prepared by using an analogous reaction protocol as described in example A2.a).

C) Preparation of Intermediate 5

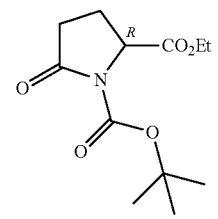

Starting from intermediate 2, intermediate 5 was prepared by using an analogous reaction protocol as described in example A2.a).

Example A3

Preparation of Intermediate 6

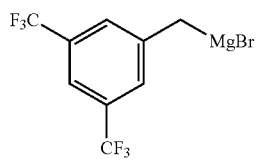

Magnesium (396 mg, 16.28 mmol) was stirred in Et$_2$O (5 ml). Then a few drops of 3,5-bis(trifluoromethyl)benzyl bromide were added. The r.m. was warmed and the reaction started. Then additional Et$_2$O (15 ml) was added and 3,5-bis(trifluoromethyl)benzyl bromide (5 g, 16.28 mmol) in Et$_2$O (20 ml) was added dropwise under spontaneous reflux. The r.m. was refluxed for 3 h and cooled to r.t. The crude product was used in the following step without further purification as intermediate 6.

Example A4

A) Preparation of Intermediate 7

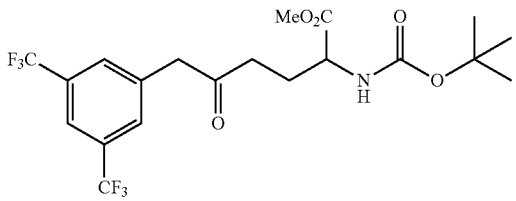 [SMILES: COC(=O)C(CCC(=O)Cc1cc(C(F)(F)F)cc(C(F)(F)F)c1)NC(=O)OC(C)(C)C]

Intermediate 3 (28 g, 108.8 mmol) was stirred in Et₂O (704 ml) under nitrogen at −50° C. Then intermediate 6 (41.47 g, 125.1 mmol) was added dropwise keeping temperature between −40° C. and −50° C. The r.m. was stirred 1 h at −40° C., warmed to 10° C. and stirred 1 h at 0-10° C. Then the r.m. was cooled to −10° C. A sat. aq. NH₄Cl sol. (60 ml) was added dropwise then water was added to dissolve all the salts. The aqueous phase was washed with Et₂O (2×100 ml). The separated organic phase was dried (MgSO₄), filtered and the organic layers combined and evaporated in vacuo. The crude product was purified by flash column chromatography (eluent: EtOAc/DCM from 0/100 to 2/98). The product fractions were collected and the solvent evaporated in vacuo. Yield: 31 g of intermediate 7 (57%).

B) Preparation of Intermediate 8

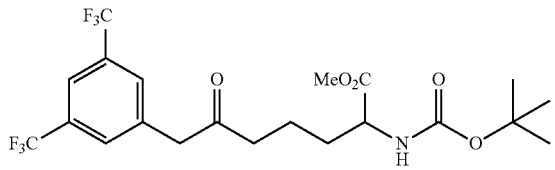 [SMILES: COC(=O)C(CCCC(=O)Cc1cc(C(F)(F)F)cc(C(F)(F)F)c1)NC(=O)OC(C)(C)C]

Starting from intermediate 4 and intermediate 6, intermediate 8 was prepared by using an analogous reaction protocol as described in example A4.a).

B) Preparation of Intermediate 9

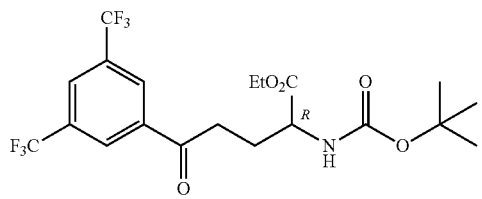

Starting from intermediate 5 and intermediate 6, intermediate 9 was prepared by using an analogous reaction protocol as described in example A4.a).

C) Preparation of Intermediate 10

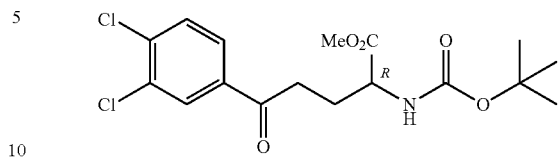

Starting from intermediate 5 and 3,4-dichlorophenylmagnesium bromide, intermediate 10 was prepared by using an analogous reaction protocol as described in example A4.a).

Example A5

A) Preparation of Intermediate 11

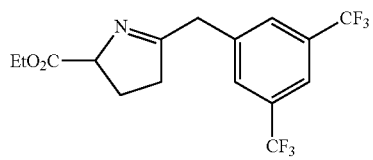 [SMILES: CCOC(=O)C1CCC(Cc2cc(C(F)(F)F)cc(C(F)(F)F)c2)=N1]

Intermediate 7 (28 g, 57.68 mmol) was stirred in DCM (850 ml) at 5° C. TFA (64 ml, 836 mmol) was added at 5° C. Then the r.m. was stirred at r.t. for 2 h. Then the r.m. was cooled and TFA (24 ml, 313 mmol) was added. Then the r.m. was stirred at r.t. for 2 h. Then the r.m. was cooled and TFA (24 ml, 313 mmol) was added. The r.m. was cooled to 5° C. and Et₃N (240 ml, 1.7 mol) was added. The r.m. was stirred at r.t. for 10 min and water was added. The aqueous phase was washed with DCM (twice). The separated organic phase was dried (MgSO₄), filtered and the organic layers combined and evaporated in vacuo. The crude product was purified by flash column chromatography (eluent: EtOAc/DCM 5/95). The product fractions were collected and the solvent evaporated in vacuo. Yield: 20 g of intermediate 11 (71%).

B) Preparation of Intermediate 12

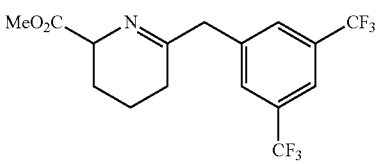 [SMILES: COC(=O)C1CCCC(Cc2cc(C(F)(F)F)cc(C(F)(F)F)c2)=N1]

Starting from intermediate 8, intermediate 12 was prepared by using an analogous reaction protocol as described in example A5.a).

C) Preparation of Intermediate 13

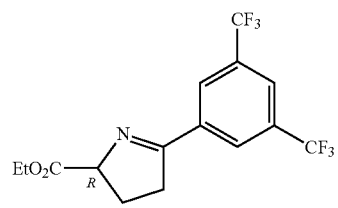

Starting from intermediate 9, intermediate 13 was prepared by using an analogous reaction protocol as described in example A5.a).

C) Preparation of Intermediate 14

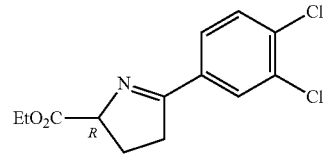

Starting from intermediate 10, intermediate 14 was prepared by using an analogous reaction protocol as described in example A5.a).

Example A6

A) Preparation of Intermediate 15

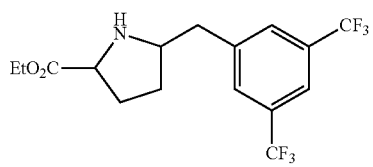 [SMILES: CCOC(=O)C1CCC(Cc2cc(C(F)(F)F)cc(C(F)(F)F)c2)N1]

HCl (37% in water) (40.93 ml, 490.1 mmol) was added to intermediate 11 (15 g, 40.8 mmol) in 2-propanol (470 ml) at 5° C. Then sodium cyanoborohydride (12.83 g, 204.2 mmol) was added portionwise at 5° C. The r.m. was stirred at r.t. for 2 h. The r.m. was poured in portionwise under cooling t<10° C. in a sat. aq. NaHCO$_3$ sol. (700 ml). The aqueous phase was washed with EtOAc (twice). The separated organic phase was dried (MgSO$_4$), filtered and the organic layers combined and evaporated in vacuo. The crude product was purified by flash column chromatography (eluent: EtOAc/DCM 10/90). The product fractions were collected and the solvent evaporated in vacuo. Yield: 8 g of intermediate 15 (53%).

B) Preparation of Intermediate 16

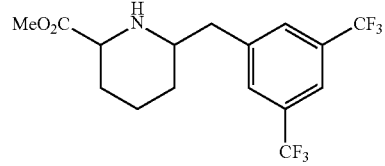 [SMILES: COC(=O)C1CCCC(Cc2cc(C(F)(F)F)cc(C(F)(F)F)c2)N1]

Starting from intermediate 12, intermediate 16 was prepared by using an analogous reaction protocol as described in example A6.a).

C) Preparation of Intermediate 17

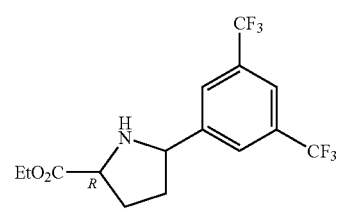

Starting from intermediate 13, intermediate 17 was prepared by using an analogous reaction protocol as described in example A6.a).

D) Preparation of Intermediate 18

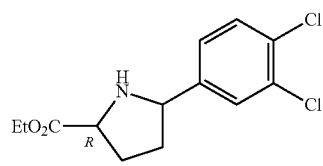

Starting from intermediate 14, intermediate 18 was prepared by using an analogous reaction protocol as described in example A6.a).

Example A7

A) Preparation of Intermediate 19

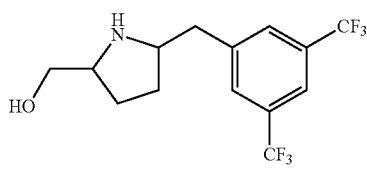

Sodium borohydride (1.84 g, 3.25 mmol) was added in small portions to stirred solution of intermediate 15 (1.2 g, 3.25 mmol) in MeOH (23 ml) cooled with an ice/EtOH bath under nitrogen. The r.m. was stirred at r.t. for 1 h. The r.m. was diluted with DCM (50 ml) and a sat. aq. NH$_4$Cl sol. (20 mL) and stirred for 30 min. The aqueous layer was extracted with DCM (3×50 ml). The separated organic phase was dried (MgSO$_4$), filtered and the organic layers combined and evaporated in vacuo. The crude product was purified by flash column chromatography (eluent: MeOH(NH$_3$)/DCM from 2.5/97.5 to 5/95). The product fractions were collected and the solvent evaporated in vacuo. Yield: 770 mg of intermediate 19 (72%).

B) Preparation of Intermediate 20

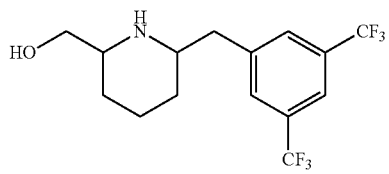

Starting from intermediate 16, intermediate 20 was prepared by using an analogous reaction protocol as described in example A7.a).

Example A8

A) Preparation of Intermediate 21

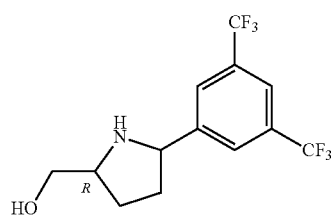

Lithium aluminum hydride (0.55 g, 14.44 mmol) was added portionwise to a cooled solution of intermediate 17 (5.13 g, 14.44 mmol) in Et$_2$O (140 ml) under nitrogen. The r.m. was stirred at 0° C. for 2 h. The r.m. was quenched with water and extracted with Et$_2$O. The separated organic phase was dried (MgSO$_4$), filtered and the organic layers combined and evaporated in vacuo. Yield: 4.5 g of intermediate 21 (99%).

B) Preparation of Intermediate 22

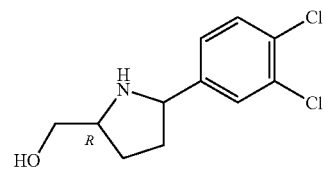

Starting from intermediate 18, intermediate 22 was prepared by using an analogous reaction protocol as described in example A8.a).

Example A9

Preparation of Intermediate 23

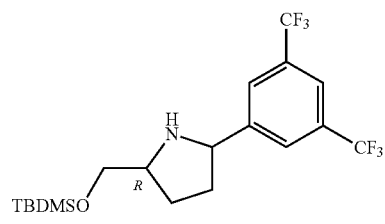

To a suspension of intermediate 21 (4.5 g, 14.37 mmol), imidazole (2.93 g, 43.1 mmol) in DCM (40 ml) was added tert-butyl-chloro-dimethylsilane (3.25 g, 21.55 mmol). The r.m. was stirred at r.t. overnight. DCM was added and the organic layer was washed with a sat. aq. NaHCO$_3$ sol. The separated organic phase was dried (MgSO$_4$), filtered and the organic layers combined and evaporated in vacuo. The crude product was purified by flash column chromatography (eluent: EtOAc/heptane from 0/100 to 20/80). The product fractions were collected and the solvent evaporated in vacuo. Yield: 3.01 g of intermediate 23 (49%/a).

Example A10

Preparation of Intermediate 24

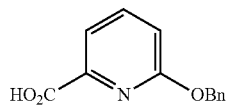 [SMILES: O=C(O)c1cccc(OCc2ccccc2)n1]

Sodium hydride (60% dispersion in mineral oil) (2.92 g, 72.98 mmol) was added to a mixture of 6-chloropyridine-2-carboxylic acid (5 g, 31.73 mmol), benzyl alcohol (4.27 ml, 41.25 mmol) in anhydrous THF (250 ml). The r.m. was stirred at reflux for 48 h. The r.m. was poured into water and extracted with EtOAc (2×75 ml). The aqueous layer was acidified to pH=2 with an aq. HCl 37% sol. and extracted with DCM (2×100 ml). The separated organic phase was dried (MgSO$_4$), filtered and the organic layers combined and evaporated in vacuo to a give a solid that was triturated with heptane. Yield: 6 g of intermediate 24 as a white solid (82%).

Example A11

A) Preparation of Intermediate 25

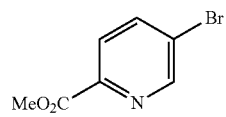

Thionyl chloride (223 ml, 3.07 mol) was added dropwise to an ice cooled 5-bromo-2-pyridinecarboxylic acid (207 g, 1.02 mol) in MeOH (1.5 l). After the addition was completed, the r.m. was stirred at reflux for 3 h. The r.m. was cooled to r.t. and evaporated in vacuo. The residue was triturated with MeCN/DIPE. Yield: 180.3 g of intermediate 25 as a white solid (81%).

B) Preparation of Intermediate 26

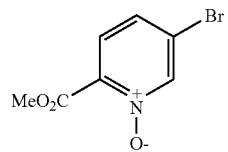

Trifluoroacetic anhydride (150 ml, 1.08 mol) was added dropwise to an ice-cooled mixture of intermediate 25 (114 g, 0.53 mol), urea hydrogen peroxide (105 g, 1.12 mol) in MeCN (0.7 l) while keeping the internal T below 10° C. The r.m. was allowed to come to r.t. and stirring was continued for 2 days. The r.m. was poured into a 0.5 M HCl sol. (1 l) and extracted with DCM (2×0.3 l). The separated organic phase was dried (MgSO$_4$), filtered and the organic layers combined and evaporated in vacuo. Yield: 120 g of intermediate 26 as a yellowish oil (98%).

C) Preparation of Intermediate 27

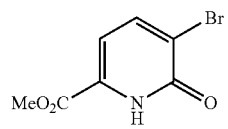

Trifluoroacetic anhydride (295 ml, 2.12 mol) was added dropwise to an ice-cooled mixture of intermediate 26 (120 g, 0.52 mol) in DMF (1 l) while keeping the internal T below 10° C. The r.m. was allowed to come to r.t. and stirring was continued for 16 h. The r.m. was evaporated in vacuo. The residue was treated with water (0.5 l) and DCM (1 l). The separated organic phase was washed with brine (0.5 l). The separated organic phase was dried (MgSO$_4$), filtered and the organic layers combined and evaporated in vacuo to give a slurry oil which was treated with water (0.2 l). An off-white solid was collected by filtration and dried. Yield: 62.5 g of intermediate 27 as an off-white solid (52%).

D) Preparation of Intermediate 28

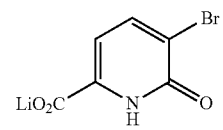

Lithium hydroxide (1.48 g, 0.062 mol) in water (30 ml) was added in one portion to intermediate 27 (13 g, 0.056 mol) in THF (100 ml). The r.m. was stirred at 60° C. for 3 days. The r.m. was evaporated in vacuo and co-evaporated with MeCN (3×50 ml). Yield: 12.5 g of intermediate 28 as an off-white solid (99%).

Example A11

A) Preparation of Intermediate 29

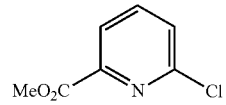

Thionyl chloride (23 ml, 0.32 mol) was added dropwise to an ice cooled 6-bromo-2-pyridinecarboxylic acid (12.23 g, 0.061 mol) in MeOH (100 ml). After the addition was completed, the r.m. was stirred at reflux for 16 h. The r.m. was cooled to r.t. and evaporated in vacuo. The residue was treated with DCM and a sat. aq. NaHCO$_3$ sol. The separated organic phase was dried (MgSO$_4$), filtered and the organic layers combined and evaporated in vacuo. Yield: 10 g of intermediate 29 as a white solid (94%).

B) Preparation of Intermediate 30

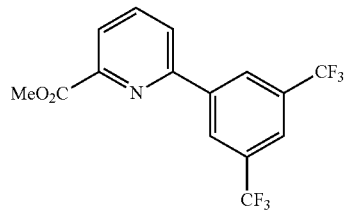 [SMILES: COC(=O)c1cccc(-c2cc(C(F)(F)F)cc(C(F)(F)F)c2)n1]

Intermediate 29 (3 g, 0.017 mol), 3,5-bis(trifluoromethyl) phenylboronic acid (5 g, 0.019 mol), potassium carbonate (5 g, 0.036 mol) in DMF (50 ml) were charged in a tube and flushed with nitrogen. Then Pd(PPh$_3$)$_4$ (1 g, 0.87 mmol) was added. The r.m. was stirred at 160° C. for 1 h. The r.m. was cooled, poured onto ice water (0.1 l) and extracted with DIPE (3×0.1 l). The combined organic layers were treated with brine (0.1 l), dried (MgSO$_4$), filtered and evaporated in vacuo. The crude product was purified by flash column chromatography (eluent: DCM/heptane from 30/70 to 50/50). The product fractions were collected and the solvent evaporated in vacuo. Yield: 4 g of intermediate 30 as a white solid (65%).

C) Preparation of Intermediate 31

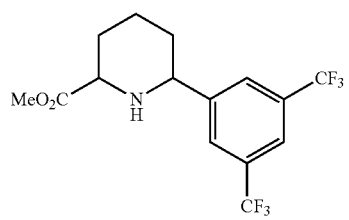 [SMILES: COC(=O)C1CCCC(c2cc(C(F)(F)F)cc(C(F)(F)F)c2)N1]

A hydrogenation flask was charged with platinum (IV) oxide (200 mg, 0.88 mmol) under nitrogen. Intermediate 30 (2.8 g, 0.008 mol) in AcOH (20 ml) was added and the flask was flushed with hydrogen. The process was repeated three times and then stirring was started until hydrogen-uptake had ceased. The r.m. was filtered over a small plug of dicalite. The filtrate was evaporated in vacuo. The residue was diluted with DCM (0.1 l) and treated with an aq. 1 M NaOH sol. until pH=7. The aqueous layer was extracted with DCM (2×50 ml). The combined organic layers were dried (MgSO$_4$), filtered and evaporated in vacuo. The crude product was purified by flash column chromatography (eluent: DCM/heptane from 30/70 to 100/0). The product fractions were collected and the solvent evaporated in vacuo. Yield: 2 g of intermediate 31 as an oil which solidified upon standing to a white solid (70%).

D) Preparation of Intermediate 32

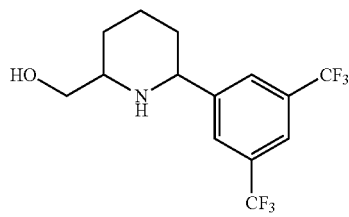

Starting from intermediate 31, intermediate 32 was prepared by using an analogous reaction protocol as described for intermediate 31.

Example A12

A) Preparation of Intermediate 33

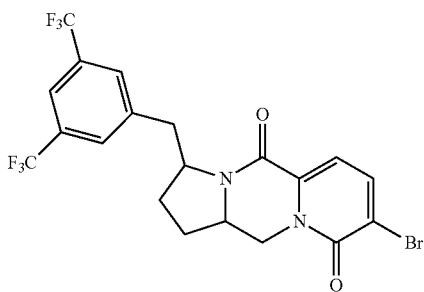 [SMILES: O=C1c2ccc(Br)c(=O)n2CC2CCC(Cc3cc(C(F)(F)F)cc(C(F)(F)F)c3)N12]

HBTU (1.27 g, 3.36 mmol) was added portionwise to a stirred solution of intermediate 28 (752 mg, 3.36 mmol), DIPEA (1.58 ml, 9.17 mmol) in DMF (60 ml) cooled with an ice/EtOH bath under nitrogen. The mixture was stirred at r.t. for 1 h. Intermediate 19 (1 g, 3.06 mmol) in DMF (60 ml) cooled with an ice/EtOH bath was added dropwise to the previous solution. The r.m. was stirred at r.t. for 24 h. Then HBTU (900 mg, 2.37 mmol) was added and the r.m. was stirred at r.t. for 24 h. The solvent was evaporated in vacuo. The residue was diluted with a sat. aq. NaHCO$_3$ sol. (150 ml) and extracted with EtOAc (250 ml). The combined organic layers were dried (MgSO$_4$), filtered and evaporated in vacuo. The crude product was purified by flash column chromatography (eluent: EtOAc/DCM from 2/98 to 5/95). The product fractions were collected and the solvent evaporated in vacuo. Yield: 900 mg of intermediate 33 (58%).

B) Preparation of Intermediates 34A/34B

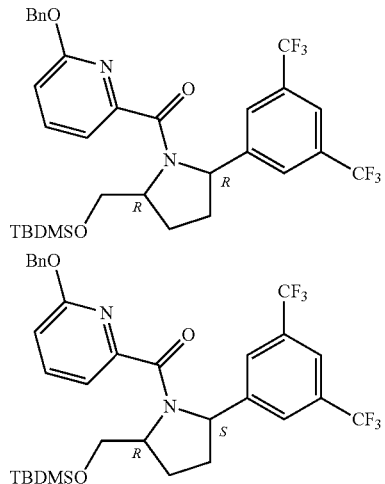

Starting from intermediate 24 and intermediate 23, intermediate 34a and intermediate 34b were prepared by using an analogous reaction protocol as described in example A12.a). The crude product was purified by flash column chromatography (eluent: EtOAc/Heptane from 0/100 to 20/80). The product fractions were collected and the solvent evaporated in vacuo. Yield: 1.19 g of intermediate 34a (26%) and 1.47 g of intermediate 34b (33%).

C) Preparation of Intermediate 35A/35B

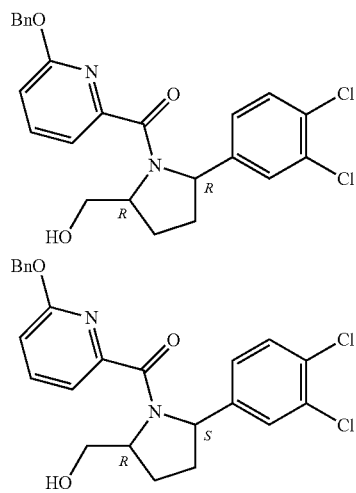

Starting from intermediate 24 and intermediate 22, intermediate 35a and intermediate 35b were prepared by using an analogous reaction protocol as described in example A12.a). The crude product was purified by flash column chromatography (eluent: EtOAc/Heptane from 0/100 to 40/60). The product fractions were collected and the solvent evaporated in vacuo. Yield: 1 g of intermediate 35a (38%) and 0.52 g of intermediate 35b (20%).

Example A13

A) Preparation of Intermediate 39

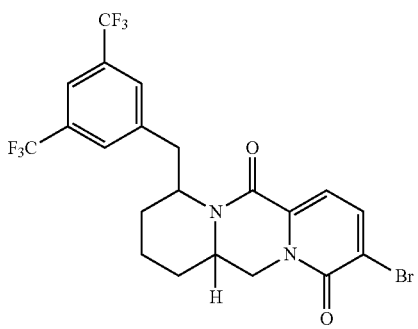 [SMILES: O=C1c2ccc(Br)c(=O)n2CC2CCCC(Cc3cc(C(F)(F)F)cc(C(F)(F)F)c3)N12]

Intermediate 20 (450 mg, 1.32 mmol) and intermediate 27 (275 mg, 1.19 mmol) were stirred at 170-180° C. for 3 h under nitrogen. The r.m. was cooled and dissolved in DCM. The crude product was purified by flash column chromatography (eluent: EtOAc/DCM from 2/98 to 5/95). The product fractions were collected and the solvent evaporated in vacuo. Yield: 300 mg of intermediate 39 (43%).

B) Preparation of Intermediate 40

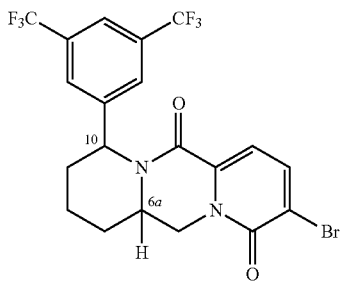 [SMILES: O=C1c2ccc(Br)c(=O)n2CC2CCCC(c3cc(C(F)(F)F)cc(C(F)(F)F)c3)N12]

Mixture of 6aR,10S and 6aS, 10R

Starting from intermediate 32 and intermediate 27, intermediate 40 (mixture of 6aR, 10S and 6aS, 10R) was prepared by using an analogous reaction protocol as described in example A13.a).

Example A14

A) Preparation of Intermediate 41A

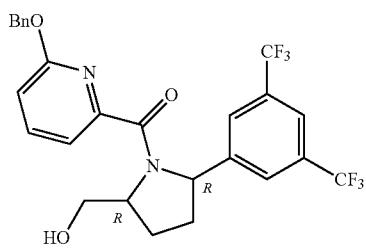

Tetra-butylammonium fluoride trihydrate (0.88 g, 2.79 mmol) was added to a solution of intermediate 34a (1.19 g, 1.86 mmol) in THF (6 ml). The r.m. was stirred at r.t. for 2 h. Water was added and the aqueous phase was extracted with EtOAc. The crude product was purified by flash column chromatography (eluent: MeOH/DCM from 0/100 to 5/95). The product fractions were collected and the solvent evaporated in vacuo. Yield: 739 mg of intermediate 41a as a yellow solid (76%).

B) Preparation of Intermediate 41B

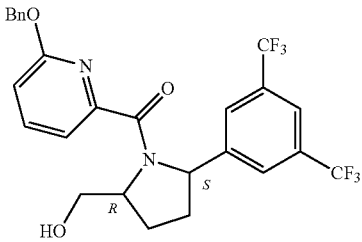

Starting from intermediate 34b, intermediate 41b was prepared by using an analogous reaction protocol as described in example A14.a).

Example A15

A) Preparation of Intermediate 42A

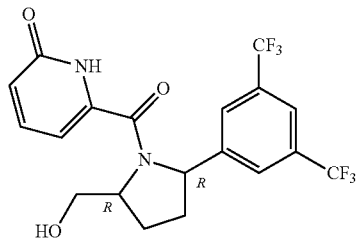

Palladium (10% wt) on active carbon wet Degussa type (74 mg) was added to a suspension of intermediate 41a (739 mg, 1.41 mmol) in MeOH (6 ml) at 0° C. The r.m. was hydrogenated at 1 atm at r.t. for 2 h. The r.m. was filtered though a pad of celite and washed with EtOH. The filtrate was evaporated in vacuo. The crude product was purified by flash column chromatography (eluent: EtOAc/DCM from 0/100 to 30/70). The product fractions were collected and the solvent evaporated in vacuo. Yield: 612 mg of intermediate 42a as a yellow solid (99%).

B) Preparation of Intermediate 42B

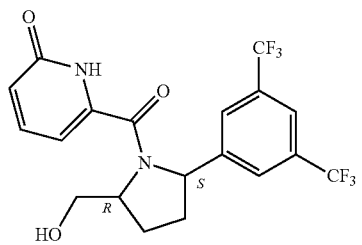

Starting from intermediate 41b, intermediate 42b was prepared by using an analogous reaction protocol as described in example A15.a).

Example A16

A) Preparation of Intermediate 43A

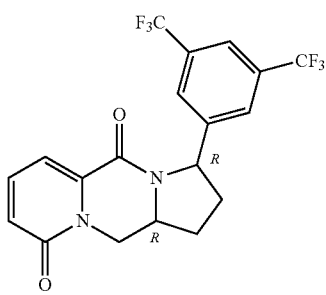

Triphenylphosphine (554 mg, 2.11 mmol) and diisopropyl azodicarboxylate (0.42 ml, 2.11 mmol) were added to a solution of intermediate 42a (612 mg, 1.41 mmol) in THF (5 ml) at 0° C. The r.m. was stirred at r.t. The solvent was evaporated in vacuo. The crude product was purified by flash column chromatography (eluent: EtOAc/heptane from 0/100 to 80/20). The product fractions were collected and the solvent evaporated in vacuo. Yield: 468 mg of intermediate 43a as a white solid (80%).

B) Preparation of Intermediate 43B

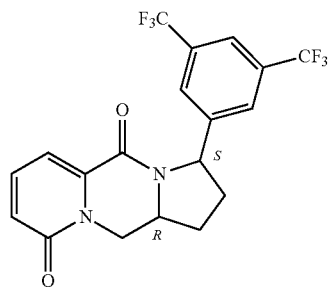

Starting from intermediate 42b, intermediate 43b was prepared by using an analogous reaction protocol as described in example A16.a).

Example A17

A) Preparation of Intermediate 44A

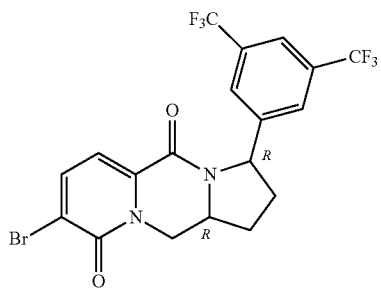

Bromine (69 ul, 1.35 mmol) was added dropwise to a stirred solution of intermediate 43a in DCM (4 ml) and AcOH (1 ml) under nitrogen. The r.m. was stirred at r.t. overnight. The r.m. was diluted with a sat. aq. NaHCO$_3$ sol. and extracted with DCM. The combined organic layers were dried (MgSO$_4$), filtered and evaporated in vacuo. The crude product was purified by flash column chromatography (silica; EtOAc/hexane from 0/100 to 50/50). The product fractions were collected and the solvent evaporated in vacuo. Yield: 300 mg of intermediate 44a as a yellow pale solid (54%).

B) Preparation of Intermediate 44B

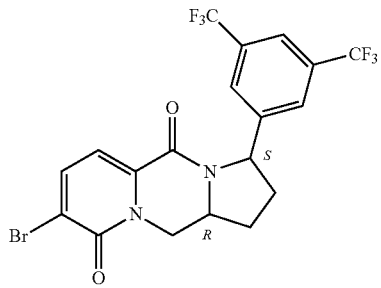

Starting from intermediate 43b, intermediate 44b was prepared by using an analogous reaction protocol as described in example A17.a).

Example A18

A) Preparation of Intermediate 45A

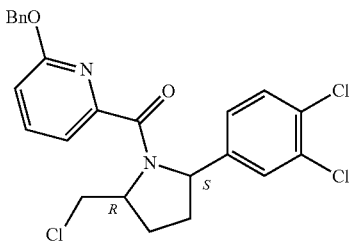

Thionyl chloride (0.14 ml, 1.92 mmol) was added to a stirred solution of intermediate 35a (0.8 g, 1.74 mmol) in DCM (20 ml) under nitrogen at 5° C. The r.m. was stirred at r.t. for 2 h. The mixture was diluted with a sat. aq. NaHCO₃ sol. and extracted with DCM. The separated organic phase was dried (MgSO₄), filtered and the solvent evaporated in vacuo. The crude product was purified by flash column chromatography (EtOAc/DCM from 0/100 to 50/50). The product fractions were collected and the solvent evaporated in vacuo. Yield: 0.43 g of intermediate 45a as a colourless oil (51%) and 0.25 g of intermediate 47a (40%).

B) Preparation of Intermediate 46A

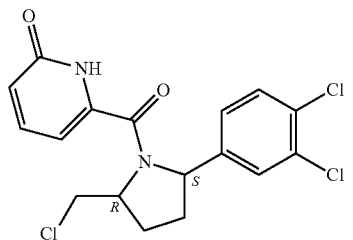

Boron tribromide (0.26 ml, 2.71 mmol) was added to a solution of intermediate 45a (0.43 g, 0.9 mmol) in DCM (10 ml). The r.m. was stirred at r.t. for 4 h. A sat. aq. NaHCO₃ sol. and MeOH were added. The r.m. was extracted with EtOAc and DCM. The separated organic phase was dried (MgSO₄), filtered and the solvent evaporated in vacuo. Yield: 0.32 g of intermediate 46a (92%).

C) Preparation of Intermediate 47A

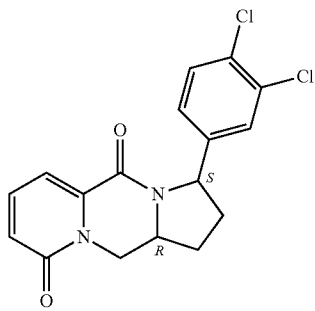

Sodium hydride (60% dispersion in mineral oil) (0.049 g, 1.24 mmol) was added to a stirred solution of intermediate 46a (0.32 g, 0.83 mmol) in DMF (20 ml) under nitrogen at 0° C. The mixture was stirred at r.t. for 45 min. The r.m. was diluted with water and extracted with EtOAc. The separated organic phase was dried (MgSO₄), filtered and the solvent evaporated in vacuo. Yield: 0.29 g of intermediate 47a as a colorless oil (100%).

D) Preparation of Intermediate 48A

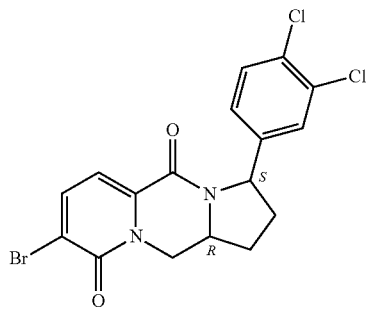

Starting from intermediate 47a, intermediate 48a was prepared by using an analogous reaction protocol as described for intermediate 47a.

B. Preparation of the Compounds

Example B1

A) Preparation of Compound 1

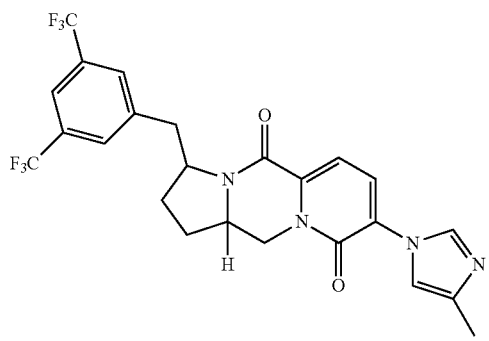 [SMILES: Cc1cn(-c2ccc3n(c2=O)CC2CCC(Cc4cc(C(F)(F)F)cc(C(F)(F)F)c4)N2C3=O)cn1]

In a first vial equipped with a magnetic stir bar and a screw cap septum, a solution of Pd₂(dba)₃ (38 mg, 0.042 mmol) and 2-di-tert-butylphosphino-3,4,5,6-tetramethyl-2',4',6'-triisopropyl 1-1,1'-biphenyl (40 mg, 0.083 mmol) in 1,4-dioxane (1.6 ml) and toluene (7.8 ml) was flushed with nitrogen and stirred at 120° C. for 3 min. A second vial, equipped with a magnetic stir bar and a screw cap septum, was charged with 4-methylimidazole (188 mg, 2.29 mmol) and potassium phosphate (884 mg, 4.16 mmol) then intermediate 33 (1.060 g, 2.08 mmol) and also flushed with nitrogen. The premixed catalyst solution was added by syringe into the second vial. The r.m. was heated at 120° C. for 5 h. The r.m. was cooled to r.t. and diluted with EtOAc (50 ml). The organic phase was washed with brine (30 ml). The separated organic phase was dried (MgSO₄), filtered and the solvent evaporated in vacuo. The crude product was purified by flash column chromatography (eluent: MeOH/DCM from 1/99 to 3/97). The product fractions were collected and the solvent evaporated in vacuo. Yield: 400 mg of compound 1 (37%).

B) Preparation of Compound 2, Compound 3, Compound 4 and Compound 5

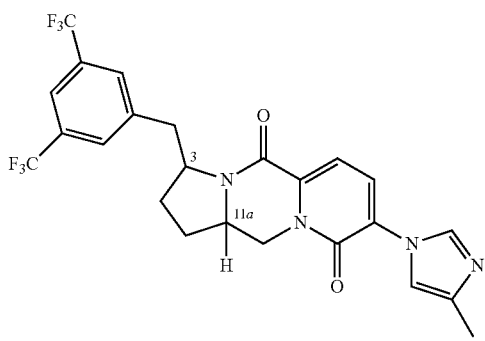 [SMILES: Cc1cn(-c2ccc3n(c2=O)CC2CCC(Cc4cc(C(F)(F)F)cc(C(F)(F)F)c4)N2C3=O)cn1]

Compound 1 (930 mg) was separated into its four stereoisomers by preparative SFC on (Chiralpak® Daicel OD 20×250 mm). Mobile phase ($CO_2$, MeOH with 0.2% $iPrNH_2$) to yield 148 mg of compound 2 (3R, 11aR) or (3S, 11aS), 115 mg of compound 3 (3S, 11aR) or (3R, 11aS), 138 mg of compound 4 (3S, 11aS) or (3R, 11aR) and 127 mg of compound 5 (3R, 11aS) or (3S, 11aR).

Example B2

A) Preparation of Compound 6

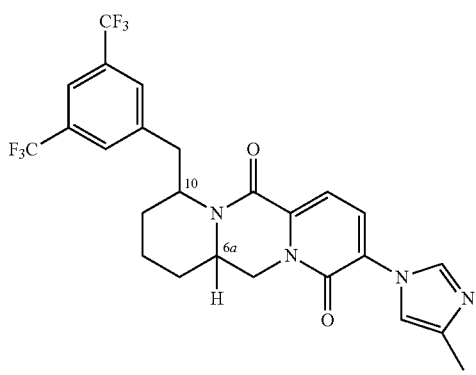

Starting from intermediate 39, compound 6 was prepared according to the procedure as described for compound 1.

B) Preparation of Compound 7, Compound 8, Compound 9 and Compound 10

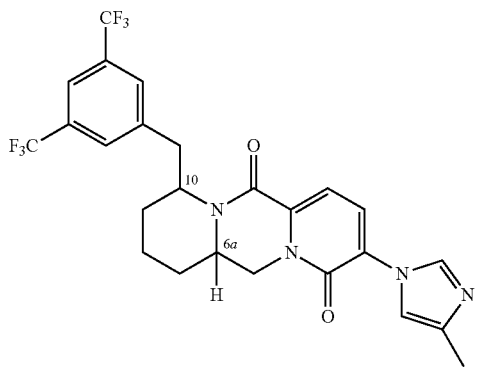

Compound 6 (1.44 g) was separated into its four stereoisomers by preparative SFC on (Chiralpak® Daicel OD 20×250 mm). Mobile phase ($CO_2$, MeOH with 0.2% $iPrNH_2$) to yield 221 mg of compound 7 (6aR, 10R) or (6aS, 10S), 217 mg of compound 8 (6aS, 10R) or (6aR, 10S), 242 mg of compound 9 (6aR, 10S) or (6aS, 10R) and 190 mg of compound 10 (6aS, 10S) or (6aR, 10R).

Example B3

A) Preparation of Compound 11

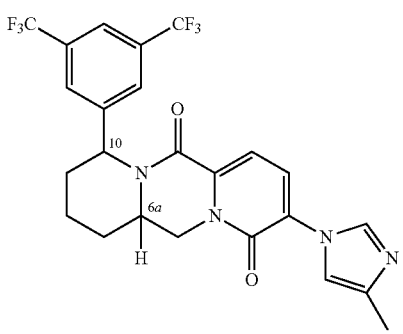

Starting from intermediate 40, compound 11 (mixture of (6aR, 10S) and (6aS, 10R)) was prepared according to the procedure as described for compound 1.

B) Preparation of Compound 12 and Compound 13

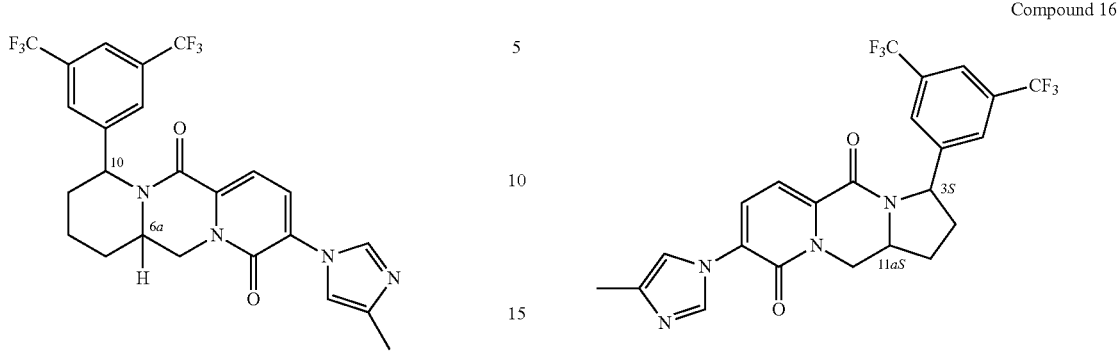

Compound 11 (400 mg, 40% purity) was separated into the corresponding enantiomers by preparative SFC on (Chiralpak® Daicel OD 20×250 mm). Mobile phase ($CO_2$, MeOH with 0.2% $iPrNH_2$) to yield 21 mg of compound 12 (6aR, 10S) or (6aS, 10R) and 19 mg of compound 13 (6aS, 10R) or (6aR, 10S).

Example B4

A) Preparation of Compound 14

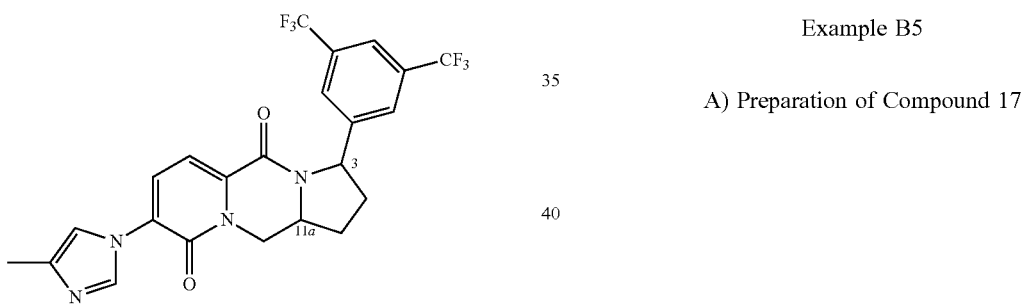

Starting from intermediate 44a, compound 14 (mixture of (3R, 11aR) and (3S, 11aS)) was prepared according to the procedure as described for compound 1.

B) Preparation of Compound 15 and Compound 16

Compound 15

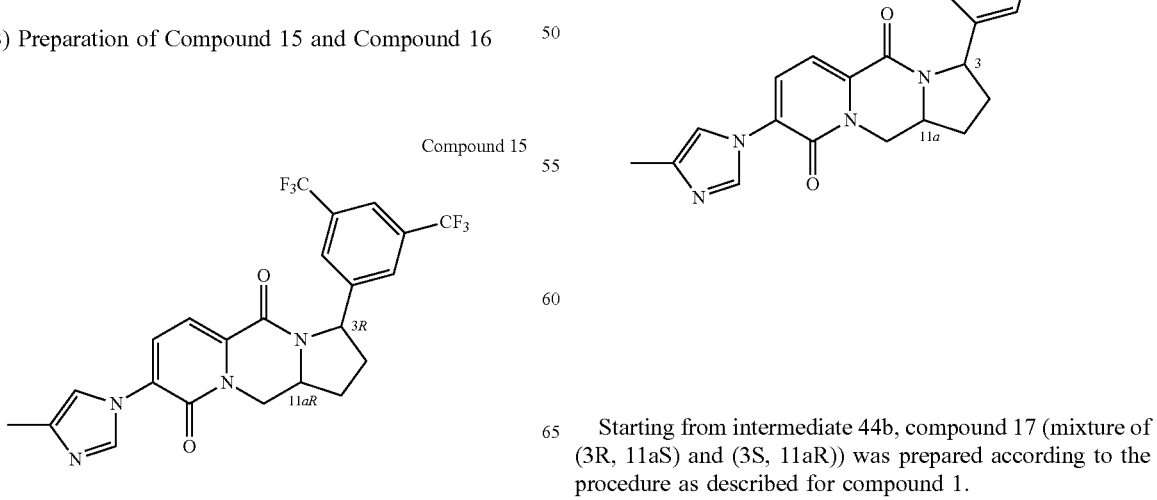

Compound 16

Compound 14 (140 mg) was separated into its corresponding enantiomers by preparative SFC on (Chiralpak® Daicel OD 20×250 mm). Mobile phase ($CO_2$, MeOH with 0.2% $iPrNH_2$) to yield 120 mg of compound 15 (3R, 11aR) and 5 mg of compound 16 (3S, 11aS).

Example B5

A) Preparation of Compound 17

Starting from intermediate 44b, compound 17 (mixture of (3R, 11aS) and (3S, 11aR)) was prepared according to the procedure as described for compound 1.

B) Preparation of Compound 18 and Compound 19

Compound 18

Compound 19

Compound 17 (225 mg) was separated into its corresponding enantiomers by preparative SFC on (Chiralpak® Daicel OD 20×250 mm). Mobile phase (CO$_2$, MeOH with 0.2% iPrNH$_2$) to yield 5 mg of compound 18 (3R, 11aS) and 160 mg of compound 19 (3S, 11aR).

Example B6

Preparation of Compound 20 and Compound 21

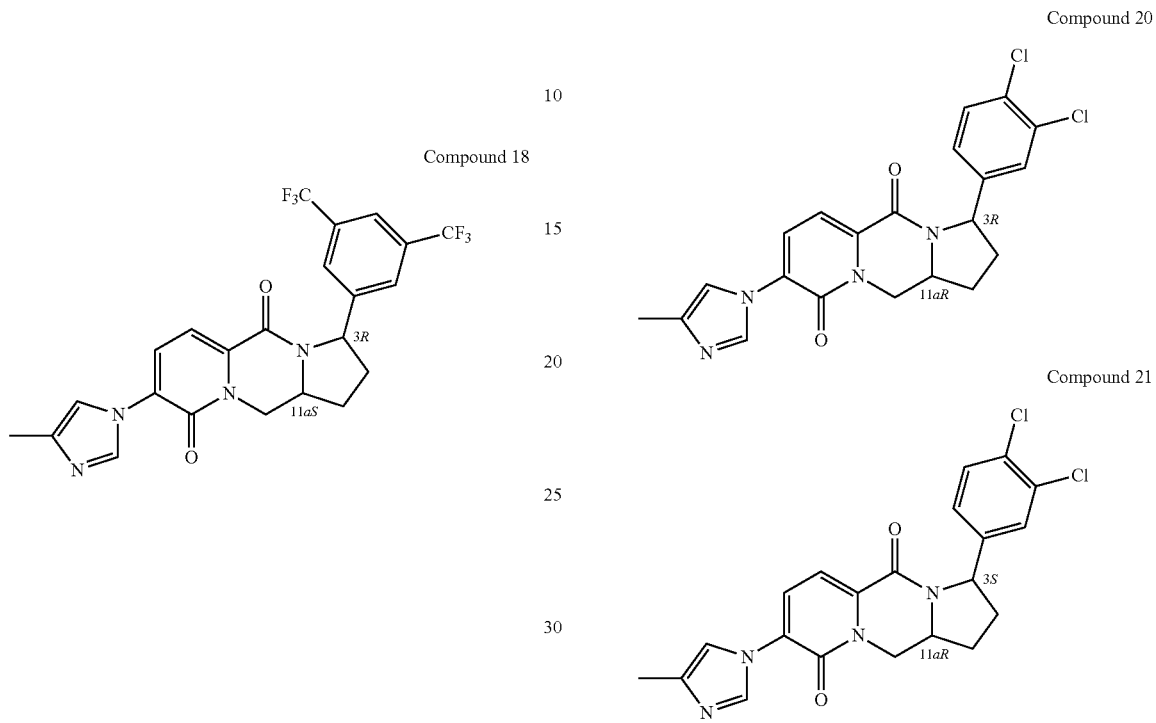

Compound 20

Compound 21

4-Methylimidazole (0.069 g, 0.84 mmol), cesium carbonate (0.27 g, 0.84 mmol) and copper iodide (0.016 g, 0.084 mmol) were added to a solution of intermediate 48a (0.18 g, 0.42 mmol) in DMF (5 ml) (previously deoxygenated). Nitrogen was bubbled through the r.m. for 5 min before it was heated in a sealed tube at 120° C. under nitrogen for 12 h. Water and EtOAc was added. The organic layer was separated and the aqueous layer was extracted with EtOAc. The organic phase was washed with brine. The separated organic phase was dried (MgSO$_4$), filtered and the solvent evaporated in vacuo. The crude product was purified by flash column chromatography (eluent: MeOH/DCM from 0/100 to 3/97). The product fractions were collected and the solvent evaporated in vacuo. The residue was triturated with MeOH/DIPE and was purified by preparative HPLC on (LUNA 5U C18 (2) 100A). Mobile phase (5 mM NH$_4$OAc/MeCN 90/10). The residues were dissolved with DCM and washed with water. The separated organic phases were dried (MgSO$_4$), filtered and the solvent evaporated in vacuo to yield 8 mg of compound 20 (3R, 11aR) and 5 mg compound 21 (3S, 11aR).

The compounds listed in Table 1 have been prepared. 'Co. No.' means compound number. The absolute stereochemical assignment for compounds 15-16, 18-19 and 20-21 was performed by NMR.

TABLE 1

| Co. No. | Structure | Stereochemistry comment | Optical Rotation (OR) |
|---|---|---|---|
| 1 | 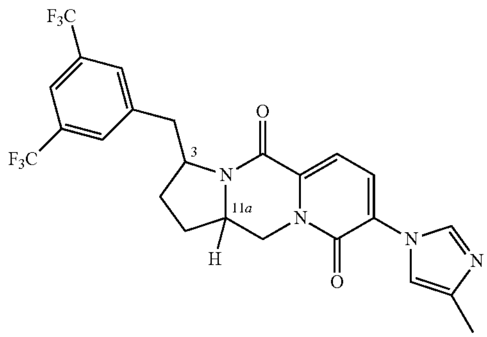 | Mixture of Co. No. 2-5 | |
| 2 | | (3R, 11aR) or (3S, 11aS) | OR: −82.73° (589 nm; 20° C.; 0.4315 w/v %; DMF) |
| 3 | | (3S, 11aR) or (3R, 11aS) | OR: −39.95° (589 nm; 20° C.; 0.3855 w/v %; DMF) |
| 4 | | (3S, 11aS) or (3R, 11aR) | OR: +81.21° (589 nm; 20° C.; 0.3805 w/v %; DMF) |
| 5 | | (3R, 11aS) or (3S, 11aR) | OR: +39.96° (589 nm; 20° C.; 0.458 w/v %; DMF) |
| 6 | 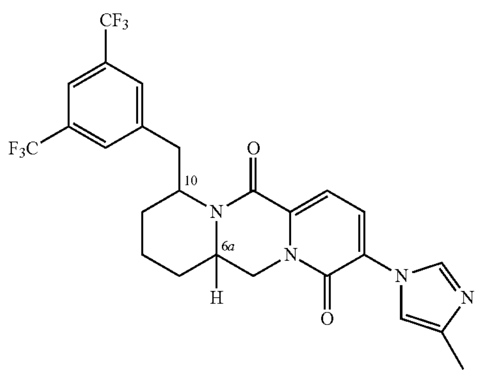 | Mixture of Co. No. 7-10 | |
| 7 | | (6aR, 10R) or (6aS, 10S) | OR: −269.02° (589 nm; 20° C.; 0.3066 w/v %; DMF) |
| 8 | | (6aS, 10R) or (6aR, 10S) | OR: −34.57° (589 nm; 20° C.; 0.3645 w/v %; DMF) |
| 9 | | (6aR, 10S) or (6aS, 10R) | OR: +34.64° (589 nm; 20° C.; 0.3435 w/v %; DMF) |
| 10 | | (6aS, 10S) or (6aR, 10R) | OR: +267.87° (589 nm; 20° C.; 0.417 w/v %; DMF) |
| 11 | 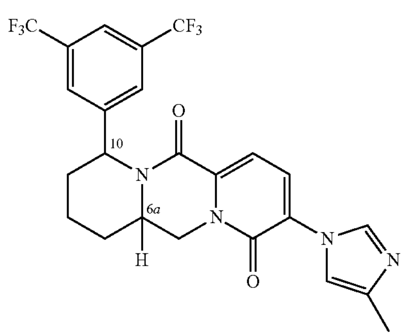 | Mixture of Co. No. 12-13 | |
| 12 | | (6aR, 10S) or (6aS, 10R) | |
| 13 | | (6aS, 10R) or (6aR, 10S) | |
| 14 | 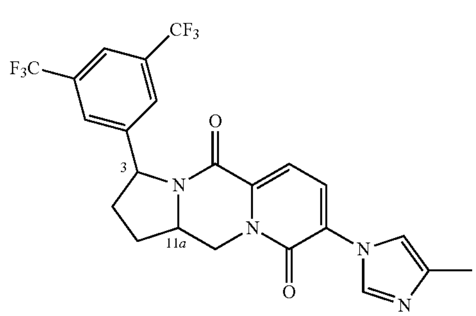 | Mixture of Co. No. 15-16 | |
| 15 | | (3R, 11aR) | |
| 16 | | (3S, 11aS) | |

TABLE 1-continued

| Co. No. | Structure | Stereochemistry comment | Optical Rotation (OR) |
|---|---|---|---|
| 17 | | Mixture of Co. No. 18-19 | |
| 18 | | (3R, 11aS) | |
| 19 | | (3S, 11aR) | |
| 20 | | (3R, 11aR) | |
| 21 | | (3S, 11aR) | |

Analytical Part
LCMS (Liquid Chromatography/Mass Spectrometry)

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software. Compounds are described by their experimental retention times ($R_t$) and ions. If not specified differently in the table of data, the reported molecular ion corresponds to the $[M+H]^+$ (protonated molecule) and/or $[M-H]^-$ (deprotonated molecule). For molecules with multiple isotopic patterns (e.g. Br or Cl), the reported value is the one obtained for the lowest isotope mass. All results were obtained with experimental uncertainties that are commonly associated with the method used.

Hereinafter, "SQD" means Single Quadrupole Detector, "BEH" means bridged ethylsiloxane/silica hybrid, "DAD" means Diode Array Detector, "HSS" means High Strength silica, "ELSD" means Evaporative Light Scanning Detector.

TABLE 2

LCMS Method codes (Flow expressed in mL/min; column temperature (Col T) in ° C.; Run time in minutes)

| Method code | Instrument | Column | Mobile phase | Gradient | Flow Col T | Run time |
|---|---|---|---|---|---|---|
| 1 | Waters: Alliance ®- DAD - ZQ and ELSD 2000 Alltech | Waters: Xterra MS C18 (3.5 µm, 4.6*100 mm) | A: 25 mM CH$_3$COONH$_4$ in 95% H$_2$O + 5% CH$_3$CN B: CH$_3$CN C: CH$_3$OH D: (40% CH$_3$CN and 40% CH$_3$OH and 20% H$_2$O with 0.25% CH$_3$COOH | From 100% A to 1% A, 49% B and 50% C in 6.5 min, to 1% A and 99% B in 0.5 min, to 100% D in 1 min held for 1.0 min to 100% A in 0.5 min and held for 1.5 min. | 1.6 40 | 11 |
| 2 | Waters: Acquity ® UPLC ® - DAD and SQD | Waters: BEH C18 (1.7 µm, 2.1*50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 55 | 2 |

TABLE 2-continued

| | LCMS Method codes (Flow expressed in mL/min; column temperature (Col T) in ° C.; Run time in minutes) | | | | | |
|---|---|---|---|---|---|---|
| Method code | Instrument | Column | Mobile phase | Gradient | Flow Col T | Run time |
| 3 | Waters: Acquity ® UPLC ® - DAD and SQD | Waters: HSS T3 (1.8 µm, 2.1*100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.8 55 | 3.5 |

Melting Points

Melting points (m.p.) were determined with a DSC823e or DSC1 (Mettler-Toledo), and were measured with a temperature gradient of 10° C./min.

The results of the analytical measurements are shown in table 2a.

TABLE 2a

Retention time (R$_t$) in min., [M + H]$^+$ peak (protonated molecule), LCMS method and m.p. (melting point in ° C.).

| Co. No. | Rt | [M + H]$^+$ | LCMS Method | m.p. (° C.) |
|---|---|---|---|---|
| 1 | 6.13 | 511 | 1 | 234.89 |
| 2 | 6.10 | 511 | 1 | 255.25 |
| 3 | 6.14 | 511 | 1 | 241.17 |
| 4 | 6.11 | 511 | 1 | 254.80 |
| 5 | 6.13 | 511 | 1 | 238.34 |
| 7 | 1.12 | 525 | 2 | 231.07 |
| 8 | 1.15 | 525 | 2 | 247.06 |
| 9 | 1.15 | 525 | 2 | 246.53 |
| 10 | 1.12 | 525 | 2 | 231.74 |
| 12 | 1.07 | 511 | 2 | n.d. |
| 13 | 1.07 | 511 | 2 | n.d. |

TABLE 2a-continued

Retention time (R$_t$) in min., [M + H]$^+$ peak (protonated molecule), LCMS method and m.p. (melting point in ° C.).

| Co. No. | Rt | [M + H]$^+$ | LCMS Method | m.p. (° C.) |
|---|---|---|---|---|
| 15 | 1.04 | 497 | 2 | n.d. |
| 16 | 1.04 | 497 | 2 | n.d. |
| 18 | 1.79 | 497 | 3 | n.d. |
| 19 | 1.83 | 497 | 3 | n.d. |

(n.d. means not determined)

NMR

For a number of compounds, $^1$H NMR spectra were recorded on a Bruker Avance III with a 300 MHz Ultrashield magnet, on a Bruker DPX-400 spectrometer operating at 400 MHz, on a Bruker DPX-360 operating at 360 MHz, or on a Bruker Avance 600 spectrometer operating at 600 MHz, using CHLOROFORM-d (deuterated chloroform, CDCl$_3$) or DMSO-d$_6$ (deuterated DMSO, dimethyl-d6 sulfoxide) as solvent. Chemical shifts (δ) are reported in parts per million (ppm) relative to tetramethylsilane (TMS), which was used as internal standard.

TABLE 2b $^1$H NMR results

| Co. No. | $^1$H NMR result |
|---|---|
| 2 | $^1$H NMR (360 MHz, DMSO-d$_6$) δ ppm 1.61-1.78 (m, 2 H) 1.95-2.07 (m, 1 H) 2.15 (s, 3 H) 2.17-2.27 (m, 1 H) 3.10 (dd, J = 13.4, 7.9 Hz, 1 H) 3.38-3.46 (m, 2 H) 3.78-3.95 (m, 1 H) 4.36-4.52 (m, 1 H) 4.99 (dd, J = 13.5, 4.0 Hz, 1 H) 6.98 (d, J = 7.7 Hz, 1 H) 7.41 (s, 1 H) 7.80 (d, J = 7.7 Hz, 1 H) 7.93 (s, 2 H) 7.96 (s, 1 H) 8.24 (s, 1 H) |
| 3 | $^1$H NMR (360 MHz, DMSO-d$_6$) δ ppm 1.51-1.69 (m, 1 H) 1.77-1.98 (m, 2 H) 2.05-2.14 (m, 1 H) 2.16 (s, 3 H) 3.01 (dd, J = 13.2, 8.8 Hz, 1 H) 3.21 (dd, J = 13.4, 12.3 Hz, 1 H) 3.37-3.40 (m, 1 H) 3.83-3.99 (m, 1 H) 4.29-4.41 (m, 1 H) 4.98 (dd, J = 13.4, 3.5 Hz, 1 H) 7.13 (d, J = 7.7 Hz, 1 H) 7.43 (s, 1 H) 7.83 (d, J = 7.7 Hz, 1 H) 7.98 (s, 2 H) 8.00 (s, 1 H) 8.26 (s, 1 H) |
| 4 | $^1$H NMR (360 MHz, DMSO-d$_6$) δ ppm 1.61-1.79 (m, 2 H) 1.94-2.08 (m, 1 H) 2.15 (s, 3 H) 2.18-2.27 (m, 1 H) 3.10 (dd, J = 13.2, 7.7 Hz, 1 H) 3.39-3.46 (m, 2 H) 3.79-3.95 (m, 1 H) 4.36-4.52 (m, 1 H) 4.99 (dd, J = 13.5, 4.0 Hz, 1 H) 6.98 (d, J = 7.7 Hz, 1 H) 7.41 (s, 1 H) 7.80 (d, J = 7.7 Hz, 1 H) 7.93 (s, 2 H) 7.96 (s, 1 H) 8.24 (s, 1 H) |
| 5 | $^1$H NMR (360 MHz, DMSO-d$_6$) δ ppm 1.45-1.70 (m, 1 H) 1.73-1.97 (m, 2 H) 2.03-2.14 (m, 1 H) 2.16 (s, 3 H) 3.01 (dd, J = 13.2, 8.8 Hz, 1 H) 3.21 (t, J = 12.8 Hz, 1 H) 3.37-3.40 (m, 1 H) 3.84-3.99 (m, 1 H) 4.28-4.41 (m, 1 H) 4.98 (dd, J = 13.5, 3.3 Hz, 1 H) 7.13 (d, J = 7.7 Hz, 1 H) 7.43 (s, 1 H) 7.83 (d, J = 7.7 Hz, 1 H) 7.98 (s, 2 H) 8.00 (s, 1 H) 8.27 (s, 1 H) |
| 7 | $^1$H NMR (360 MHz, DMSO-d$_6$) δ ppm 1.26-1.43 (m, 1 H) 1.51-1.77 (m, 3 H) 1.79-1.95 (m, 1 H) 1.95-2.06 (m, 1 H) 2.15 (s, 3 H) 3.00-3.20 (m, 2 H) 3.59 (dd, J = 14.3, 10.2 Hz, 1 H) 4.11 (ddt, J = 14.4, 7.3, 3.8, 3.8 Hz, 1 H) 4.72 (dd, J = 13.9, 4.0 Hz, 1 H) 4.84-4.95 (m, 1 H) 6.70 (d, J = 7.7 Hz, 1 H) 7.37 (s, 1 H) 7.72 (d, J = 7.7 Hz, 1 H) 7.88 (s, 1 H) 7.96 (s, 2 H) 8.22 (d, J = 1.1 Hz, 1 H) |

TABLE 2b-continued

1H NMR results

| Co. No. | 1H NMR result |
|---|---|
| 8 | 1H NMR (360 MHz, DMSO-$d_6$) δ ppm 1.52-1.62 (m, 1 H) 1.65-1.89 (m, 3 H) 1.90-2.06 (m, 2 H) 2.15 (d, J = 0.7 Hz, 3 H) 3.02-3.26 (m, 2 H) 3.52 (dd, J = 13.9, 11.3 Hz, 1 H) 3.86-4.08 (m, 1 H) 4.27-4.44 (m, 1 H) 4.72 (dd, J = 13.9, 3.7 Hz, 1 H) 7.07 (d, J = 7.7 Hz, 1 H) 7.41 (s, 1 H) 7.80 (d, J = 8.1 Hz, 1 H) 7.96 (s, 1 H) 8.05 (s, 2 H) 8.26 (d, J = 1.1 Hz, 1 H) |
| 9 | 1H NMR (360 MHz, DMSO-$d_6$) δ ppm 1.52-1.62 (m, 1 H) 1.65-1.89 (m, 3 H) 1.90-2.06 (m, 2 H) 2.15 (s, 3 H) 3.09-3.22 (m, 2 H) 3.52 (dd, J = 13.9, 11.3 Hz, 1 H) 3.91-4.06 (m, 1 H) 4.27-4.43 (m, 1 H) 4.72 (dd, J = 13.9, 3.7 Hz, 1 H) 7.07 (d, J = 8.1 Hz, 1 H) 7.41 (s, 1 H) 7.80 (d, J = 7.7 Hz, 1 H) 7.96 (s, 1 H) 8.05 (s, 2 H) 8.26 (d, J = 1.1 Hz, 1 H) |
| 10 | 1H NMR (400 MHz, DMSO-$d_6$) δ ppm 1.27-1.43 (m, 1 H) 1.53-1.76 (m, 3 H) 1.81-1.95 (m, 1 H) 1.96-2.06 (m, 1 H) 2.15 (d, J = 0.8 Hz, 3 H) 2.99-3.21 (m, 2 H) 3.60 (dd, J = 13.9, 10.3 Hz, 1 H) 4.00-4.20 (m, 1 H) 4.72 (dd, J = 14.1, 4.0 Hz, 1 H) 4.82-4.97 (m, 1 H) 6.71 (d, J = 7.7 Hz, 1 H) 7.36 (t, J = 0.8 Hz, 1 H) 7.71 (d, J = 7.7 Hz, 1 H) 7.87 (s, 1 H) 7.96 (s, 2 H) 8.22 (d, J = 1.2 Hz, 1 H) |
| 12 | 1H NMR (600 MHz, CHLOROFORM-d) δ ppm 1.59-1.81 (m, 3 H), 2.01 (dtd, J = 14.5, 7.2, 7.2, 5.7 Hz, 1 H), 2.06-2.13 (m, 1 H), 2.23-2.28 (m, 1 H), 2.29 (s, 3 H), 3.62 (dd, J = 14.4, 11.7 Hz, 1 H), 3.97 (tt, J = 11.9, 3.3 Hz, 1 H), 5.02 (dd, J = 14.4, 3.1 Hz, 1 H), 5.18 (dd, J = 7.0, 5.1 Hz, 1 H), 7.14 (s, 1 H), 7.24 (d, J = 7.8 Hz, 1 H), 7.45 (d, J = 7.8 Hz, 1 H), 7.72 (s, 2 H), 7.78 (s, 1 H), 8.26 (d, J = 1.0 Hz, 1 H) |
| 13 | 1H NMR (360 MHz, CHLOROFORM-d) δ ppm 1.58-1.85 (m, 3 H) 1.92-2.15 (m, 2 H) 2.19-2.38 (m, 1 H) 2.29 (s, 3 H) 3.62 (dd, J = 14.3, 11.7 Hz, 1 H) 3.98 (tdd, J = 11.8, 11.8, 3.5, 3.3 Hz, 1 H) 5.02 (dd, J = 14.5, 3.1 Hz, 1 H) 5.17 (dd, J = 7.0, 5.1 Hz, 1 H) 7.14 (s, 1 H) 7.24 (d, J = 7.7 Hz, 1 H) 7.45 (d, J = 7.7 Hz, 1 H) 7.72 (s, 2 H) 7.78 (s, 1 H) 8.27 (s, 1 H) |
| 15 | 1H NMR (360 MHz, CHLOROFORM-d) δ ppm 1.89-2.07 (m, 2 H) 2.29 (d, J = 0.7 Hz, 3 H) 2.42-2.59 (m, 1 H) 2.60-2.78 (m, 1 H) 3.36 (dd, J = 13.9, 12.1 Hz, 1 H) 4.29-4.43 (m, 1 H) 5.27-5.34 (m, 1 H) 5.44 (dd, J = 13.7, 3.8 Hz, 1 H) 7.08-7.15 (m, 2 H) 7.43 (d, J = 7.7 Hz, 1 H) 7.66 (s, 2 H) 7.81 (s, 1 H) 8.23 (d, J = 1.1 Hz, 1 H) |
| 16 | 1H NMR (360 MHz, CHLOROFORM-d) δ ppm 1.89-2.09 (m, 2 H) 2.29 (s, 3 H) 2.39-2.60 (m, 1 H) 2.61-2.79 (m, 1 H) 3.36 (dd, J = 13.7, 11.9 Hz, 1 H) 4.28-4.44 (m, 1 H) 5.23-5.34 (m, 1 H) 5.45 (dd, J = 13.9, 4.0 Hz, 1 H) 7.07-7.15 (m, 2 H) 7.43 (d, J = 7.7 Hz, 1 H) 7.66 (s, 2 H) 7.81 (s, 1 H) 8.23 (s, 1 H) |
| 18 | 1H NMR (360 MHz, CHLOROFORM-d) δ ppm 1.93-2.16 (m, 2 H) 2.30 (s, 3 H) 2.35-2.43 (m, 1 H) 2.48-2.65 (m, 1 H) 3.56 (dd, J = 13.9, 12.4 Hz, 1 H) 4.03-4.17 (m, 1 H) 5.34-5.47 (m, 2 H) 7.15 (s, 1 H) 7.26 (d, J = 7.7 Hz, 1 H) 7.45 (d, J = 7.7 Hz, 1 H) 7.67 (s, 2 H) 7.81 (s, 1 H) 8.25 (s, 1 H) |
| 19 | 1H NMR (400 MHz, CHLOROFORM-d) δ ppm 1.93-2.17 (m, 2 H) 2.29 (d, J = 1.2 Hz, 3 H) 2.32-2.43 (m, 1 H) 2.49-2.65 (m, 1 H) 3.56 (dd, J = 13.7, 12.1 Hz, 1 H) 4.02-4.17 (m, 1 H) 5.37 (d, J = 9.3 Hz, 1 H) 5.41 (dd, J = 14.1, 3.6 Hz, 1 H) 7.14 (s, 1 H) 7.26 (d, J = 7.7 Hz, 1 H) 7.45 (d, J = 7.7 Hz, 1 H) 7.67 (s, 2 H) 7.81 (s, 1 H) 8.25 (d, J = 0.8 Hz, 1 H) |
| 20 | 1H NMR (300 MHz, DMSO-$d_6$) δ ppm 1.65-1.93 (m, 2 H) 2.16 (s, 3 H) 2.22-2.37 (m, 1 H) 2.44-2.50 (m, 1 H) 3.53 (t, J = 12.8 Hz, 1 H) 4.32-4.52 (m, 1 H) 5.02-5.21 (m, 2 H) 6.93 (d, J = 7.6 Hz, 1 H) 7.31 (dd, J = 8.2, 1.6 Hz, 1 H) 7.40 (s, 1 H) 7.52-7.64 (m, 2 H) 7.76 (d, J = 7.7 Hz, 1 H) 8.23 (s, 1 H) |
| 21 | 1H NMR (300 MHz, DMSO-$d_6$) δ ppm 1.70-1.93 (m, 2 H) 2.06-2.24 (m, 1 H) 2.16 (s, 3 H) 2.32-2.44 (m, 1 H) 3.72-3.88 (m, 1 H) 4.03-4.14 (m, 1 H) 5.09 (dd, J = 13.6, 3.3 Hz, 1 H) 5.17 (d, J = 9.2 Hz, 1 H) 7.05 (d, J = 7.7 Hz, 1 H) 7.32 (dd, J = 8.3, 2.0 Hz, 1 H) 7.42 (s, 1 H) 7.54 (d, J = 8.4 Hz, 1 H) 7.60 (d, J = 1.9 Hz, 1 H) 7.79 (d, J = 7.7 Hz, 1 H) 8.26 (s, 1 H) |

SFC-MS

For SFC-MS, an analytical SFC system from Berger Instruments (Newark, Del., USA) was used comprising a dual pump control module (FCM-1200) for delivery of $CO_2$ and modifier, a thermal control module for column heating (TCM2100) with temperature control in the range 1-150° C. and column selection valves (Valco, VICI, Houston, Tex., USA) for 6 different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

Co. No. 2-5: SFC-MS was carried out on a OD-H column (250×4.6 mm) (Daicel Chemical Industries Ltd) with a flow rate of 3 ml/min. Two mobile phases (mobile phase A: $CO_2$; mobile phase B: iPrOH containing 0.2% $iPrNH_2$) were employed. 50% B was hold for 25 min. Column temperature was set at 30° C. Under these conditions, Co. No. 2 eluted first from the column, Co. No. 3 eluted second from the column, Co. No. 5 eluted third from the column, and Co. No. 4 had the longest retention time (R) on the column. The measurement was compared against the mixture of the 4 compounds.

Co. No. 7-10: SFC-MS was carried out on a OD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. 25% B was hold for 15 min. Column temperature was set at 30° C. Under these conditions, Co. No. 7 eluted first from the column, Co. No. 9 eluted second from the column, Co. No. 10 eluted third from the column, and Co. No. 8 had the longest retention time ($R_t$) on the column. The measurement was compared against the mixture of the 4 compounds.

Co. No. 12-13: SFC-MS was carried out on a OD-H column (250×4.6 mm) (Daicel Chemical Industries Ltd) with a flow rate of 3 ml/min. Two mobile phases (mobile phase A: $CO_2$; mobile phase B: MeOH containing 0.2% $iPrNH_2$) were employed. First 20% B was hold for 18.5 min. Then a gradient was applied from 20% B to 50% B in 3 min, and 50% B was hold for 3.1 min. Column temperature was set at 30° C. Under these conditions, Co. No. 12 had a shorter retention time (R) on the column than Co. No. 13.

Co. No. 15-16: SFC-MS was carried out on a AD-H column (250×4.6 mm) (Daicel Chemical Industries Ltd) with a flow rate of 3 ml/min. Two mobile phases (mobile phase A: $CO_2$; mobile phase B: EtOH containing 0.2% $iPrNH_2$) were employed. First a gradient was applied from 10% B to 40% B in 18.75 min. Subsequently, a gradient was applied from 40% B to 50% B in 2 min, and 50% B was hold for 3.6 min. Column temperature was set at 30° C. Under these conditions, Co. No. 15 had a shorter retention time ($R_t$) on the column than Co. No. 16.

Co. No. 18-19: SFC-MS was carried out on a AD-H column (250×4.6 mm) (Daicel Chemical Industries Ltd) with a flow rate of 3 ml/min. Two mobile phases (mobile phase A: $CO_2$; mobile phase B: EtOH containing 0.2% $iPrNH_2$) were employed. First a gradient was applied from 10% B to 40% B in 18.75 min. Subsequently, a gradient was applied from 40% B to 50% B in 2 min, and 50% B was hold for 3.6 min. Column temperature was set at 30° C. Under these conditions, Co. No. 18 had a shorter retention time ($R_t$) on the column than Co. No. 19.

Pharmacology

A) Screening of the Compounds of the Invention for γ-Secretase-Modulating Activity Screening was carried out using SKNBE2 human neuroblastoma cells carrying the hAPP 695-wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) and streptomycin 50 µg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 µg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 3, the data are calculated as percentage of the maximum amount of amyloid Beta 42 measured in the absence of the test compound.

The sigmoidal dose response curves were analyzed using non-linear regression analysis with percentage of the control plotted against the log concentration of the compound. A 4-parameter equation was used to determine the $IC_{50}$.

TABLE 3

| Co. No. | IC50 Aβ42 (µM) | IC50 Aβtotal (µM) | Co. No | IC50 Aβ42 (µM) | IC50 Aβtotal (µM) |
|---|---|---|---|---|---|
| 20 | 4.47 | 9.33 | 4 | 0.05 | >10 |
| 21 | 1.32 | >15.14 | 5 | 0.98 | >10 |
| 12 | 0.24 | >10 | 18 | >10 | >10 |
| 13 | >10 | >10 | 16 | 0.19 | >10 |
| 15 | 4.57 | >10 | 7 | 1.12 | >10 |
| 19 | 0.72 | >10 | 8 | 0.11 | >10 |
| 1 | 0.16 | >10 | 9 | 0.29 | >10 |
| 2 | >10 | >10 | 10 | 0.13 | 3.16 |
| 3 | 0.42 | >10 | | | |

("n.d." means not determined)

B) Demonstration of In Vivo Efficacy

B-1) Aβ42

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Animals treated with the Aβ42 lowering agent were examined and compared to those untreated or treated with vehicle and brain levels of soluble Aβ42, Aβ40, Aβ38, and Aβ37 were quantitated by Meso Scale Discovery's (MSD) electrochemiluminescence detection technology. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After 4 h, the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (Meso Scale Discovery, Gaithersburg, Md.).

The SULFO-TAG emits light upon electrochemical stimulation initiated at the electrode. MSD Sector instrument SI6000 was used for signal read-out.

In this model a Aβ42 lowering compared to untreated animals would be advantageous, in particular a Aβ42 lowering with at least 10%, more in particular a Aβ42 lowering with at least 20%.

B-2) Aβ38

Aβ38 increasing agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ38 increasing agents can be administered in any standard form using any standard method. For example, but not limited to, Aβ38 increasing agents can be in the form of liquid, tablets or capsules that are taken orally or by injection. Aβ38 increasing agents can be administered at any dose that is sufficient to significantly increase levels of Aβ38 in the blood, plasma, serum, cerebrospinal fluid (CSF), or brain.

To determine whether acute administration of an Aβ38 increasing agents would increase Aβ38 levels in vivo, non-transgenic rodents, e.g. mice or rats were used. Animals treated with the Aβ38 increasing agents were examined and compared to those untreated or treated with vehicle and brain levels of soluble Aβ42, Aβ40, Aβ38, and Aβ37 were quantitated by MSD electrochemiluminescence detection technology. Treatment periods varied from hours (h) to days and were adjusted based on the results of the Aβ38 increase once a time course of onset of effect could be established.

A typical protocol for measuring Aβ38 increase in vivo is shown but it is only one of many variations that could be used to optimize the levels of detectable Aβ. For example, Aβ38 increasing agents were formulated in 20% of Captisol® (a sulfobutyl ether of β-cyclodextrin) in water or 20% hydroxypropyl β cyclodextrin. The Aβ38 increasing agents were administered as a single oral dose or by any acceptable route of administration to overnight fasted animals. After 4 h, the animals were sacrificed and Aβ38 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 20800×g for 5 min and supernatants collected. Supernatants were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβ.

To quantify the amount of Aβ42, Aβ40, Aβ38, and Aβ37 in the soluble fraction of the brain homogenates, simultaneous specific detection of Aβ42, Aβ40, Aβ38, and Aβ37 was performed using MSD's electro-chemiluminescence multiplex detection technology. In this assay purified monoclonal antibodies specific for Abeta37 (JRD/Aβ37/3), Abeta38 (J&JPRD/Aβ38/5), Abeta40 (JRF/cAβ40/28), and Abeta42 (JRF/cAβ42/26) were coated on MSD 4-plex plates. Briefly, the standards (a dilution of synthetic Aβ42, Aβ40, Aβ38, and Aβ37) were prepared in 1.5 ml Eppendorf tube in Ultraculture, with final concentrations ranging from 10000 to 0.3 pg/m. The samples and standards were co-incubated with Sulfo-tag labelled JRF/rAβ/2 antibody to the N-terminus of Aβ as detector antibody. 50 μl of conjugate/sample or conjugate/standards mixtures were then added to the antibody-coated plate. The plate was allowed to incubate overnight at 4° C. in order to allow formation of the antibody-amyloid complex. Following this incubation and subsequent wash steps the assay was finished by adding read buffer according to the manufacturer's instructions (MesoScale Discovery, Gaitherburg, Md.).

The SULFO-TAG emits light upon electrochemical stimulation initiated at the electrode. MSD Sector instrument SI6000 was used for signal read-out.

In this model a Aβ38 increase compared to untreated animals would be advantageous, in particular a Aβ38 increase with at least 10%, more in particular a Aβ38 increase with at least 20%.

B-3) Results

The results are shown in Table 4 (dose 30 mg/kg oral dosing) (value for untreated animals as control (Ctrl) was set at 100):

| Co. No. | Aβ40 (% vs Ctrl) _Mean | Aβ42 (% vs Ctrl) _Mean | Aβ38 (% vs Ctrl) _Mean |
|---|---|---|---|
| 4 | 69 | 47 | 136 |

Prophetic Composition Examples

"Active ingredient" (a.i.) as used throughout these examples relates to a compound of Formula (I), including any tautomer or stereoisomeric form thereof, or a pharmaceutically acceptable addition salt or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

The invention claimed is:

1. A compound of Formula (I)

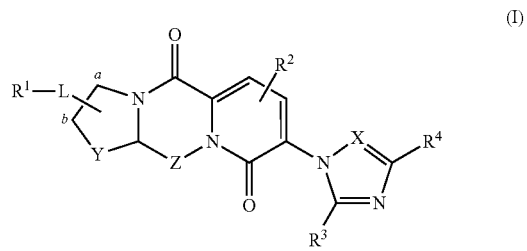

wherein
R$^1$ is phenyl, napthyl, indolyl, benzothienyl, benzothiazolyl or benzofuranyl;
  each optionally substituted with one, two or three substituents each independently selected from the group consisting of halo and C$_{1-4}$alkyl optionally substituted with one, two or three halo substituents;
L is attached at position a or b;
  L is selected from the group consisting of a covalent bond, —C$_{1-6}$-alkanediyl- and —O—C$_{1-6}$alkanediyl-;
Y is -Q-(CH$_2$)$_m$—, —CH$_2$-Q-CH$_2$—, —(CH$_2$)$_n$—,
  —(CH$_2$)$_n$— wherein one —CH$_2$— is substituted with hydroxy and C$_{1-4}$alkyl, or
  —(CH$_2$)$_n$— wherein one —CH$_2$— is substituted with one hydroxy;
n is 1, 2 or 3;
m is 1 or 2;
Q is O or NR$^6$;
R$^6$ is hydrogen or C$_{1-4}$alkyl;
Z is methylene or 1,2-ethanediyl, wherein methylene or 1,2-ethanediyl is optionally substituted with one or two C$_{1-4}$alkyl substituents;
R$^2$ is hydrogen, halo or C$_{1-4}$alkyl;
R$^3$ is hydrogen or C$_{1-4}$alkyl;
R$^4$ is hydrogen, halo or C$_{1-4}$alkyl;
X is CR$^5$; and
R$^5$ is hydrogen or C$_{1-4}$alkyl;
or a pharmaceutically acceptable salt, stereoisomer or tautomer thereof.

2. The compound according to claim 1, wherein
R$^1$ is phenyl, napthyl or indolyl;
  each optionally substituted with one, two or three substituents each independently selected from the group consisting of halo and C$_{1-4}$alkyl optionally substituted with one, two or three halo substituents;
L is attached at position a:
Z is methylene:
R$^2$ is hydrogen; and
X is CH.

3. The compound according to claim 1, wherein
R$^1$ is phenyl substituted with two substituents each independently selected from the group consisting of halo and C$_{1-4}$alkyl optionally substituted with three halo substituents;
L is attached at position a;
  L is selected from the group consisting of a covalent bond and —C$_{1-6}$alkanediyl-;
Y is —(CH$_2$)$_n$—;
n is 1 or 2;

Z is methylene;
R² is hydrogen;
R³ is hydrogen;
R⁴ is C₁₋₄alkyl; and
X is CH.

4. The compound according to claim 1, wherein
L is selected from the group consisting of a covalent bond and —C₁₋₆alkanediyl-.

5. The compound according to claim 1, wherein
R¹ is phenyl substituted with one, two or three substituents each independently selected from the group consisting of halo and C₁₋₄alkyl substituted with one, two or three halo substituents.

6. The compound according to claim 1, wherein
Z is methylene.

7. The compound according to claim 1, wherein the compound is
3-[[3,5-bis(trifluoromethyl)phenyl]methyl]-2,3,11,11a-tetrahydro-8-(4-methyl-1H-imidazol-1-yl)-1H-pyrido[1,2-a]pyrrolo[1,2-d]pyrazine-5,9-dione,
or a pharmaceutically acceptable salt, stereoisomer or tautomer thereof.

8. A pharmaceutical composition comprising a pharmaceutically acceptable carrier and, as active ingredient, a therapeutically effective amount of a compound according to claim 1.

9. A method of modulating gamma secretase activity in a subject having a disease or condition selected from the group consisting of Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid, comprising administering to a subject in need thereof, a therapeutically effective amount of a compound according to claim 1.

10. The method according to claim 9, wherein the disease is Alzheimer's disease.

11. A method of modulating gamma secretase activity in a subject having a disease or condition selected from the group consisting of neurocognitive disorder due to Alzheimer's disease, neurocognitive disorder due to traumatic brain injury, neurocognitive disorder due to Lewy body disease, neurocognitive disorder due to Parkinson's disease and vascular neurocognitive disorder, comprising administering to a subject in need thereof, a therapeutically effective amount of a compound according to claim 1.

12. A method of modulating gamma secretase activity in a subject having a disease or condition selected from the group consisting of Alzheimer's disease, traumatic brain injury, mild cognitive impairment, senility, dementia, dementia with Lewy bodies, cerebral amyloid angiopathy, multi-infarct dementia, dementia pugilistica, Down's syndrome, dementia associated with Parkinson's disease and dementia associated with beta-amyloid, comprising administering to a subject in need thereof, a therapeutically effective amount of the pharmaceutical composition of claim 8.

13. The method according to claim 12, wherein the disease is Alzheimer's disease.

14. A method of modulating gamma secretase activity in a subject having a disease or condition selected from the group consisting of neurocognitive disorder due to Alzheimer's disease, neurocognitive disorder due to traumatic brain injury, neurocognitive disorder due to Lewy body disease, neurocognitive disorder due to Parkinson's disease and vascular neurocognitive disorder, comprising administering to a subject in need thereof, a therapeutically effective amount of a pharmaceutical composition according to claim 8.

* * * * *